(12) United States Patent
Ren et al.

(10) Patent No.: US 12,023,349 B2
(45) Date of Patent: Jul. 2, 2024

(54) **METHOD FOR EXTRACTING *LACTARIUS HATSUDAKE TANAKA* POLYSACCHARIDE COMPOUND**

(71) Applicant: CENTRAL SOUTH UNIVERSITY OF FORESTRY AND TECHNOLOGY, Hunan (CN)

(72) Inventors: Jiali Ren, Hunan (CN); Qiao Yang, Hunan (CN); Songlin Chang, Hunan (CN); Yiming Tian, Hunan (CN); Hui Zhang, Hunan (CN); Yiming Zhou, Hunan (CN)

(73) Assignee: CENTRAL SOUTH UNIVERSITY OF FORESTRY AND TECHNOLOGY, Hunan (CN)

( * ) Notice: Subject to any disclaimer, the term of this patent is extended or adjusted under 35 U.S.C. 154(b) by 0 days.

(21) Appl. No.: 18/454,333

(22) Filed: Aug. 23, 2023

(65) Prior Publication Data
US 2024/0156855 A1    May 16, 2024

(30) Foreign Application Priority Data
Oct. 20, 2022    (CN) .......................... 202211286616.0

(51) Int. Cl.
*A61K 31/715*   (2006.01)
*A61K 36/07*    (2006.01)
*C08B 37/00*    (2006.01)

(52) U.S. Cl.
CPC ............. *A61K 31/715* (2013.01); *A61K 36/07* (2013.01); *C08B 37/0003* (2013.01); *A61K 2236/15* (2013.01); *A61K 2236/333* (2013.01); *A61K 2236/39* (2013.01); *A61K 2236/51* (2013.01); *A61K 2236/53* (2013.01)

(58) Field of Classification Search
CPC .............. A61K 31/715; A61K 36/07; A61K 2236/333; A61K 2236/53; C08B 37/0003
See application file for complete search history.

(56) References Cited

FOREIGN PATENT DOCUMENTS

CN    115572333 A    1/2023
JP    2010018607 A * 1/2010

OTHER PUBLICATIONS

Google Patents English machine translation of JP 2010018607 A. (Year: 2024).*
Tako et al., Carbohydrate Polymers, 2013, 92, p. 2135-2140. (Year: 2013).*
Zhang et al., Food & Machinery, 2022, 38(5), p. 143-148, published Jun. 30, 2022, English abstract only. (Year: 2023).*
The State Intellectual Property Office of People's Republic of China, Notification to Grant Patent Right for Invention, Application No. 202211286616.0, dated May 17, 2023, English Translation 2 pages.
The State Intellectual Property Office of People's Republic of China, Notification to Grant Patent Right for Invention, Application No. 202211286616.0, dated May 17, 2023, 1 page.

* cited by examiner

*Primary Examiner* — Jonathan S Lau
(74) *Attorney, Agent, or Firm* — Ziegler IP Law Group

(57) ABSTRACT

The present disclosure provides a method for extracting a *Lactarius hatsudake* Tanaka polysaccharide compound, and relates to the field of active substance extraction. This method includes: carrying out freeze-drying, pulverization, degreasing, water extraction, deproteinization, alcohol precipitation, and resin adsorption in sequence on *Lactarius hatsudake* Tanaka fruiting bodies to obtain a *Lactarius hatsudake* Tanaka refined polysaccharide mixture; to the *Lactarius hatsudake* Tanaka refined polysaccharide mixture, adding anhydrous ethanol dropwise to perform alcohol precipitation purification, and gradually collecting precipitates, to obtain *Lactarius hatsudake* Tanaka polysaccharide-10/40/60/80 active ingredients; and performing preparation via liquid chromatography on the *Lactarius hatsudake* Tanaka polysaccharide-10/40/60/80 active ingredients respectively, followed by dialysis and post-treatment to obtain *Lactarius hatsudake* Tanaka polysaccharide LHP-1, *Lactarius hatsudake* Tanaka polysaccharide LHP-2, *Lactarius hatsudake* Tanaka polysaccharide LHP-3, *Lactarius hatsudake* Tanaka polysaccharide LHP-4, and *Lactarius hatsudake* Tanaka polysaccharide LHP-5.

9 Claims, 18 Drawing Sheets

METHOD FOR EXTRACTING *LACTARIUS HATSUDAKE TANAKA* POLYSACCHARIDE COMPOUND

TECHNICAL FIELD

The present disclosure relates to the field of active substance extraction, in particular to a method for extracting a *Lactarius hatsudake* Tanaka polysaccharide compound.

BACKGROUND ART

*Lactarius hatsudake* Tanaka is subordinate to Basidiomycotina, Hymenomycetes, Agaricales, Russulaceae, and *Lactarius*, and is mainly distributed in East Asian region. It is a nutritious and precious edible fungus for eating and medicinal use.

Studies have shown that *Lactarius hatsudake* Tanaka contains a large number of active ingredients such as amino acids, vitamins, and saccharides.

To separate new active ingredients from *Lactarius hatsudake* Tanaka and study is of quite important significance for deep development of *Lactarius hatsudake* Tanaka.

SUMMARY

The present disclosure aims at providing a method for extracting a *Lactarius hatsudake* Tanaka polysaccharide compound, so as to solve the above problems.

In order to achieve the above objective, the present disclosure adopts the following technical solutions.

A method for extracting a *Lactarius hatsudake* Tanaka polysaccharide compound, including:
carrying out freeze-drying, pulverization, degreasing, water extraction, deproteinization, alcohol precipitation, and resin adsorption in sequence on *Lactarius hatsudake* Tanaka fruiting bodies to obtain a *Lactarius hatsudake* Tanaka refined polysaccharide mixture;
to the *Lactarius hatsudake* Tanaka refined polysaccharide mixture, adding anhydrous ethanol dropwise to perform alcohol precipitation purification, and gradually collecting precipitates with ethanol volume concentration of 10%, 40%, 60%, and 80%, to obtain *Lactarius hatsudake* Tanaka polysaccharide-10/40/60/80 active ingredients;
performing preparation via liquid chromatography on the *Lactarius hatsudake* Tanaka polysaccharide-10/40/60/80 active ingredients respectively, followed by dialysis and post-treatment to obtain *Lactarius hatsudake* Tanaka polysaccharide LHP-1, *Lactarius hatsudake* Tanaka polysaccharide LHP-2, *Lactarius hatsudake* Tanaka polysaccharide LHP-3, *Lactarius hatsudake* Tanaka polysaccharide LHP-4, and *Lactarius hatsudake* Tanaka polysaccharide LHP-5.

Condition of the preparation via liquid chromatography includes: an injection volume is 1 mL, a chromatography column is SUGAR-BRT-102 gel chromatography column, a column temperature is 35° C., a column length is 28 cm, a flow rate is 1.3 mL/min, and a mobile phase is 0.2 mol/L of aqueous sodium chloride solution.

A structural formula of the *Lactarius hatsudake* Tanaka polysaccharide LHP-1 is:

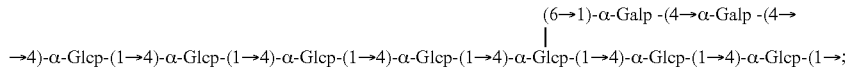

a structural formula of the *Lactarius hatsudake* Tanaka polysaccharide LHP-2 is:

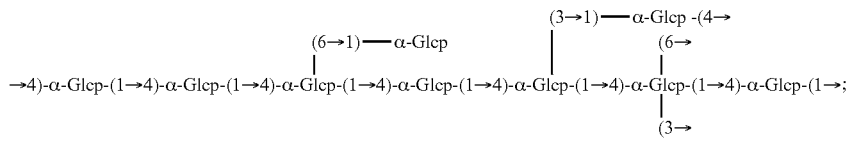

a structural formula of the *Lactarius hatsudake* Tanaka polysaccharide LHP-3 is:

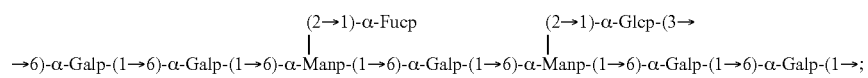

a structural formula of the *Lactarius hatsudake* Tanaka polysaccharide LHP-4 is:

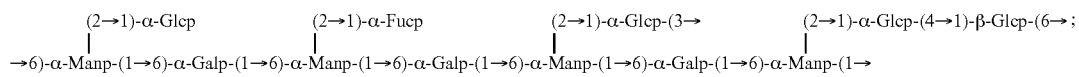

a structural formula of the *Lactarius hatsudake* Tanaka polysaccharide LHP-5 is:

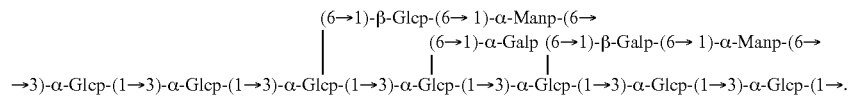

Preferably, the method satisfies at least one of the following conditions:

a. the freeze-drying is performed at a temperature of −80° C. for 2-3 d;

b. particles obtained from the pulverization have a particle size less than or equal to 60 mesh;

c. the degreasing includes: repeatedly soaking the particles obtained from the pulverization using anhydrous ethanol, collecting a solid after solid-liquid separation, drying the solid and then pulverizing the dried solid again, and sieving the resultant with a 60-mesh sieve to obtain a pretreated *Lactarius hatsudake* Tanaka freeze-dried powder;

d. the water extraction includes: mixing the degreased solid with water, treating the mixture under a condition of 85-100° C. for 3 h, after solid-liquid separation, repeating the foregoing operations on the solid, combining liquids to obtain a crude polysaccharide aqueous solution, and concentrating the crude polysaccharide aqueous solution to obtain a concentrated crude polysaccharide aqueous solution.

Preferably, the deproteinization includes: treating the solution obtained from the water extraction with papain and a Sevag reagent, placing the liquid into an 8000-14000 Da dialysis bag to stand at 4° C. for 2-3 days, during which time water is changed every 2 h, and after dialysis, concentrating the resultant to obtain a deproteinized concentrated solution.

Preferably, the alcohol precipitation includes: to the solution obtained from the deproteinization, adding 4 times volume of ethanol dropwise, followed by standing and centrifuging to obtain a polysaccharide precipitate, re-dissolving the precipitate by adding water, followed by concentrating under reduced pressure, and freeze-drying to obtain *Lactarius hatsudake* Tanaka secondary polysaccharide.

Preferably, the resin adsorption includes: dissolving the solid obtained from the alcohol precipitation in water, then adding activated JK008 macroporous resin, performing stirring and adsorbing on the mixture for 6-12 h, after solid-liquid separation, centrifuging for liquid to remove insolubles, followed by reduced-pressure distillation, secondary alcohol precipitation, and freeze-drying to obtain the *Lactarius hatsudake* Tanaka refined polysaccharide mixture.

Preferably, in the process of performing the alcohol precipitation purification, after dropwise addition for each concentration gradient is finished, the resultant is stood for 12 h at 4° C., and centrifuged to obtain the precipitate.

Preferably, the precipitate is re-dissolved by adding water and then concentrated under reduced pressure and freeze-dried to obtain the *Lactarius hatsudake* Tanaka polysaccharide-10/40/60/80 active ingredients.

Preferably, before performing the preparation via liquid chromatography, the method further includes:

mixing the *Lactarius hatsudake* Tanaka polysaccharide-10/40/60/80 active ingredients respectively with water, undergoing 60° C. water bath for 30 min, followed by vortex blending, and filtration with a 0.45 μm water film to obtain corresponding samples.

Preferably, the dialysis includes: performing dialysis for 2 d using a 7000 Da dialysis bag.

Preferably, the post-treatment includes: performing rotary evaporation and freeze-drying on the polysaccharide solution obtained after the dialysis to obtain a corresponding compound.

Compared with the prior art, the present disclosure includes the following beneficial effects.

The method for extracting a *Lactarius hatsudake* Tanaka polysaccharide compound provided in the present disclosure, taking the *Lactarius hatsudake* Tanaka fruiting bodies as raw material, performs freeze-drying (removing moisture), pulverization (improving an extraction rate), pretreatment (removing impurities such as pigments and small molecular substances), water extraction (obtaining water-soluble crude polysaccharide), deproteinization, alcohol precipitation (removing impurities such as pigments and small molecular substances), and resin adsorption (removing impurities) to obtain the *Lactarius hatsudake* Tanaka refined polysaccharide mixture, then performs the alcohol precipitation purification to obtain four parts of active ingredients, and finally performs the preparation via liquid chromatography (performing grading according to molecular weight to obtain a single component), dialysis (desalination), and post-treatment to obtain a target compound.

In the present disclosure, using this method, the *Lactarius hatsudake* Tanaka polysaccharide LHP-1, the *Lactarius hatsudake* Tanaka polysaccharide LHP-2, the *Lactarius hatsudake* Tanaka polysaccharide LHP-3, the *Lactarius hatsudake* Tanaka polysaccharide LHP-4, and the *Lactarius hatsudake* Tanaka polysaccharide LHP-5 are extracted for the first time from the *Lactarius hatsudake* Tanaka fruiting bodies, and the foregoing compounds have a good anti-tumor effect.

The *Lactarius hatsudake* Tanaka polysaccharide mixture obtained from the *Lactarius hatsudake* Tanaka freeze-dried powder has the yield of 4.7% and the purity of 85-91%; and the yields of the finally obtained LHP1/2/3/4/5 are 0.13%, 1.41%, 0.24%, 0.564%, and 0.17% respectively.

BRIEF DESCRIPTION OF DRAWINGS

In order to more clearly illustrate the technical solutions of the examples of the present disclosure, the drawings that need to be used in the examples will be introduced briefly. It should be understood that the following drawings merely show some examples of the present disclosure, and should not be considered as limiting the scope of the present disclosure.

DETAILED DESCRIPTION OF EMBODIMENTS

Figure 1:
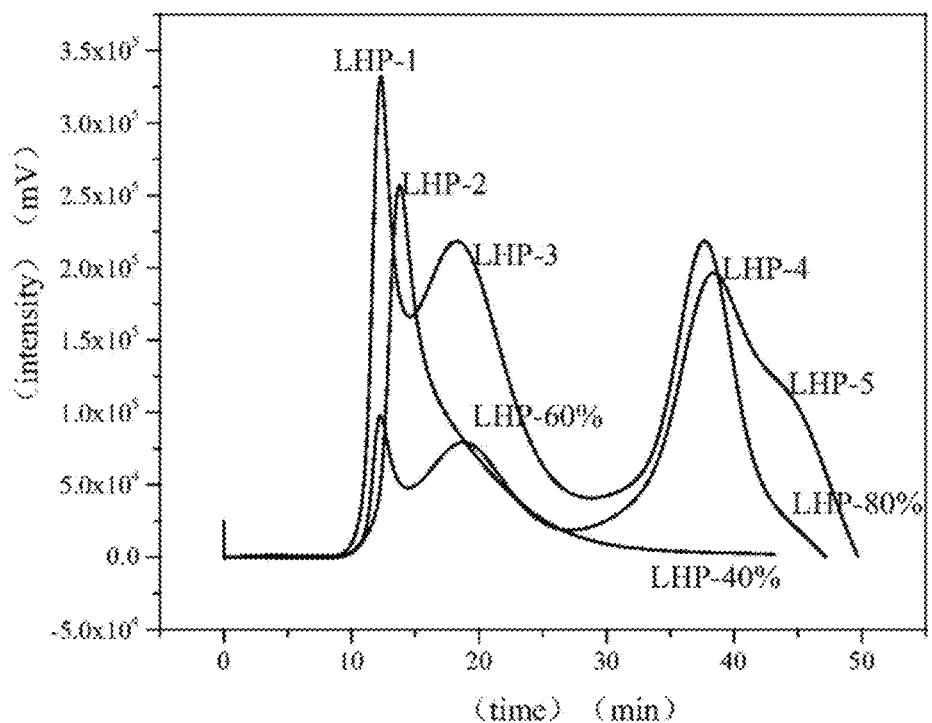
FIG. 1 shows curves performing liquid phase preparation in Example 1.

Embodiments of the present disclosure will be described in detail below with reference to specific examples, while a person skilled in the art could understand that the following examples are merely used for illustrating the present disclosure, but should not be considered as limitation on the scope of the present disclosure.

Example 1

The present example provided a method for extracting a *Lactarius hatsudake* Tanaka polysaccharide compound, specifically including the following steps.

(1) Preparation of a *Lactarius hatsudake* Tanaka polysaccharide mixture:

freeze-drying: *Lactarius hatsudake* Tanaka fruiting bodies were wiped up, pedicle-removed, and dried in a freeze-drier for 2 days;

pulverization: the freeze-dried *Lactarius hatsudake* Tanaka fruiting bodies were taken to be pulverized, and sieved with a 60-mesh sieve, to obtain a *Lactarius hatsudake* Tanaka freeze-dried powder;

degreasing: 300 g of the *Lactarius hatsudake* Tanaka powder was taken into a 5000 mL beaker, and added with 3000 mL of anhydrous ethanol, the mixture stood at room temperature for 12 h, and underwent suction filtration, supernatant was concentrated under reduced temperature at 60° C. to recover ethanol, the above operations were repeated on filter cake for 3 times in total, and finally the filter cake was collected, and dried with cold air, the dried filter cake was pulverized with a pulverizer, and sieved with a 60-mesh sieve, to obtain a pre-treated *Lactarius hatsudake* Tanaka freeze-dried powder;

water extraction: 300 g of the pre-treated *Lactarius hatsudake* Tanaka freeze-dried powder was taken into a reaction kettle, and added with 6000 mL of ultrapure water, the mixture was stirred in water bath under a condition of 85° C. for 3 h, the mixed solution was filtered first with a gauze to separate filter residue and water solution, the obtained water solution was further centrifuged at 5000 rap for 15 min, filter residue was collected and the above operations were repeated, and the supernatant was collected twice and combined into a crude polysaccharide aqueous solution, followed by concentrating under reduced pressure to 1500 mL;

deproteinization: to the concentrated crude polysaccharide aqueous solution, 3 g of papain was added, the mixture reacted at 60° C. for 1 h, and after reaction was finished, the resultant was heated to 100° C. for inactivation for 10 min, and protein was removed by centrifugation at 10000 rap for 20 min, supernatant was collected, ¼ volume of Sevag-reagent (chloroform: n-butanol=4:1) was added, after 20 min of magnetic stirring and reaction, centrifugation was carried out at 10000 rap for 20 min, upper-layer aqueous phase was taken, intermediate protein precipitate and lower-layer organic phase were removed, and the operations were repeated for 5 times until no protein precipitate was formed; the polysaccharide aqueous solution was concentrated under reduced pressure at 60° C. to remove organic phase, the resultant was subjected to rotary evaporation by repeatedly adding water, until the system was free of organic matter, and the collected supernatant was placed into a 14000 Da dialysis bag to stand at 4° C. for 2 days, during which time water was changed every 2 h, and the dialyzed solution was concentrated under reduced pressure to 600 mL;

alcohol precipitation: to the above water extraction concentrate, 4 times volume of ethanol was added, with the speed being adjusted to drop by drop by the separating funnel, and meanwhile magnetic stirring was used to ensure that each drop of ethanol was uniformly scattered into the whole solution system, the resultant stood at 4° C. for 12 h, and centrifuged at 10000 rap for 10 min, the polysaccharide precipitate was re-dissolved with addition of water, concentrated under reduced pressure at 60° C. to remove ethanol, and the concentrate was freeze-dried to obtain *Lactarius hatsudake* Tanaka secondary polysaccharide;

resin adsorption: 30 mg of the *Lactarius hatsudake* Tanaka secondary polysaccharide was taken to dissolve in 3000 mL of ultrapure water, and added with 500 g of activated JK008 macroporous resin, the mixture was stirred for adsorption for 6 h, filtered with a gauze to separate resin and polysaccharide aqueous solution, centrifuged at 10000 rap for 20 min to remove insolubles, and concentrated under reduced pressure at 60° C., followed by alcohol precipitation, and freeze-drying to obtain a *Lactarius hatsudake* Tanaka polysaccharide mixture.

(2) Preparation of *Lactarius hatsudake* Tanaka polysaccharide-1/2/3/4/5:

alcohol precipitation purification: 1 g of the *Lactarius hatsudake* Tanaka polysaccharide mixture was taken to dissolve in 200 mL of ultrapure water, and added with anhydrous ethanol dropwise until concentration of the system was 10%, the resultant was stood for 12 h at 4° C., and centrifuged to obtain a *Lactarius hatsudake* Tanaka polysaccharide-10 precipitate; supernatant was collected, anhydrous ethanol continued to be added until the concentration of the system was 40%, the resultant was stood for 12 h at 4° C., and centrifuged to obtain a *Lactarius hatsudake* Tanaka polysaccharide-40 precipitate; supernatant was collected, anhydrous ethanol continued to be added until the concentration of the system was 60%, the resultant was stood for 12 h at 4° C., and centrifuged to obtain a *Lactarius hatsudake* Tanaka polysaccharide-60 precipitate; supernatant was collected, anhydrous ethanol continued to be added until the concentration of the system was 80%, the resultant was stood for 12 h at 4° C., and centrifuged to obtain a *Lactarius hatsudake* Tanaka polysaccharide-80 precipitate; the polysaccharide was re-dissolved, concentrated under reduced pressure, and freeze-dried to obtain *Lactarius hatsudake* Tanaka polysaccharide-10/40/60/80 active ingredients; and preparation via liquid chromatogram and purification: 100 mg of the *Lactarius hatsudake* Tanaka polysaccharide-10/40/60/80 active ingredients were taken into a 5 mL EP tube, and added with 2 mL of ultrapure water, and the mixture was placed in 60° C. water bath for 30 min, then subjected to vortex blending, and filtered with a 0.45 water film; an injection volume was 1 mL, a chromatography column was SUGAR-BRT-102 gel chromatography column, a detector was Shimadzu RID-10A differential refraction index detector, a mobile phase was 0.2 mol/L aqueous sodium chloride solution, a flow rate was 1.3 mL/min, the collected elution components were dialyzed by a 7000 Da dialysis bag for 2 days, the dialyzed polysaccharide solution was subjected to rotary evaporation and freeze-dried to obtain the *Lactarius hatsudake* Tanaka polysaccharides LHP-1/2/3/4/5, and results are as shown in FIG. 1 (wherein time corresponding to the five compounds was 12.28, 13.78, 18.22, 38.419, and 43.89 min respectively).

In order to further illustrate the structure of the resulting polysaccharide compounds, structure characterization of the *Lactarius hatsudake* Tanaka polysaccharide LHP-1/2/3/4/5 is specifically as follows.

Figure 2:
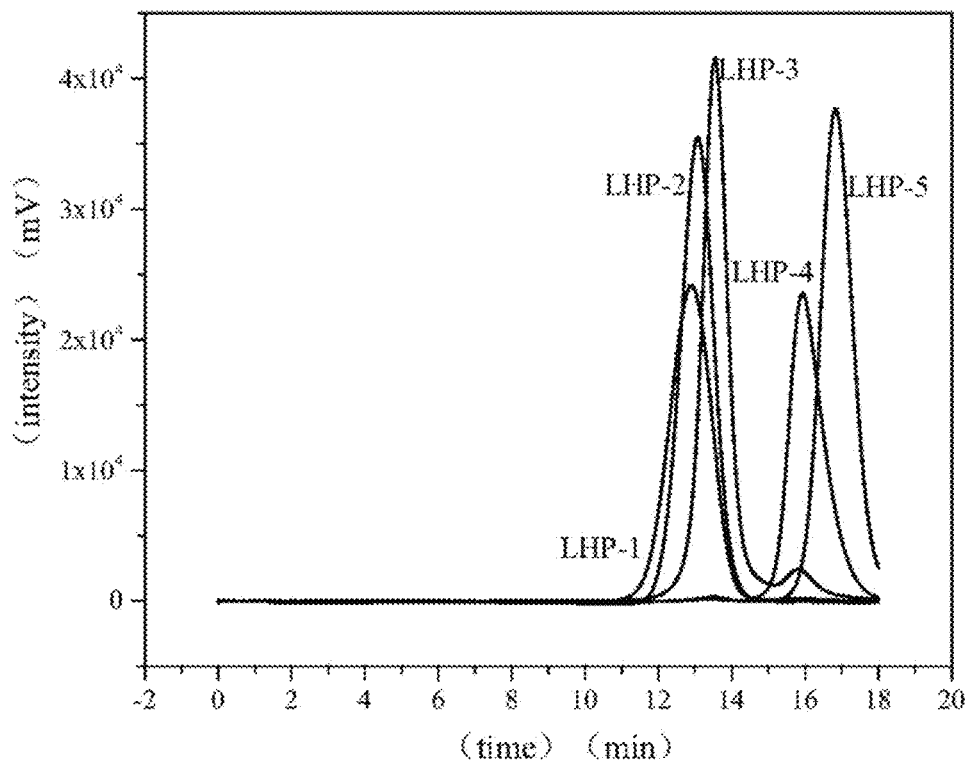
FIG. 2 shows molecular weight test curves.
Figure 3:
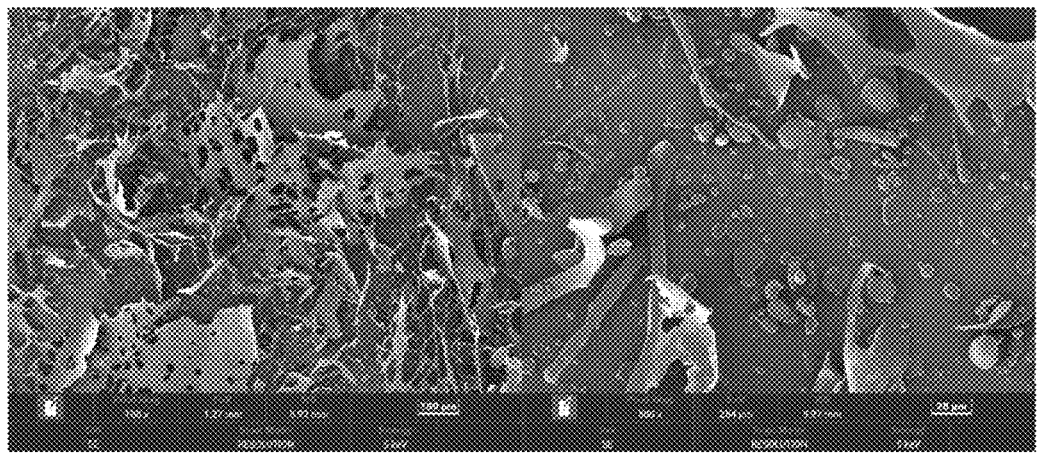
FIG. 3 is a scanning electron microscopy photograph of *Lactarius hatsudake* Tanaka polysaccharide LHP-1.
Figure 4:
FIG. 4 is a scanning electron microscopy photograph of *Lactarius hatsudake* Tanaka polysaccharide LHP-2.
Figure 5:
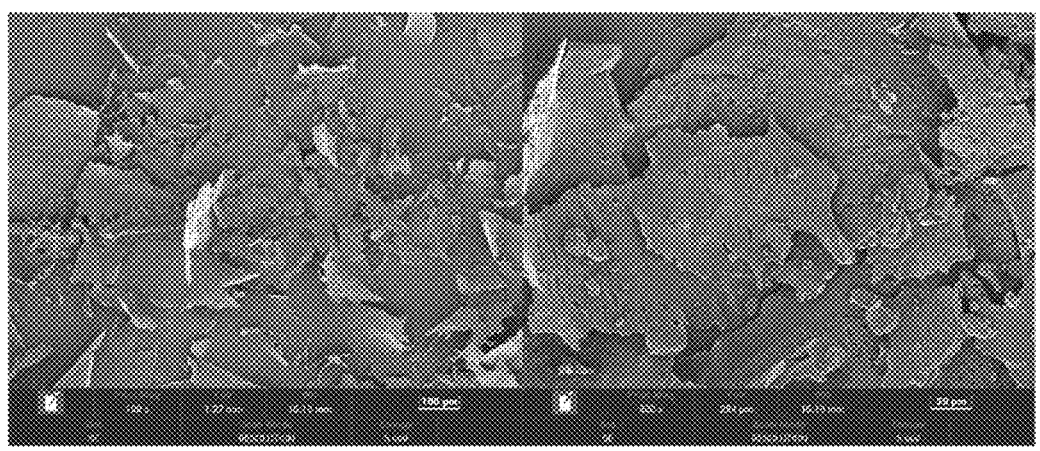
FIG. 5 is a scanning electron microscopy photograph of *Lactarius hatsudake* Tanaka polysaccharide LHP-3.
Figure 6:
FIG. 6 is a scanning electron microscopy photograph of *Lactarius hatsudake* Tanaka polysaccharide LHP-4.
Figure 7:
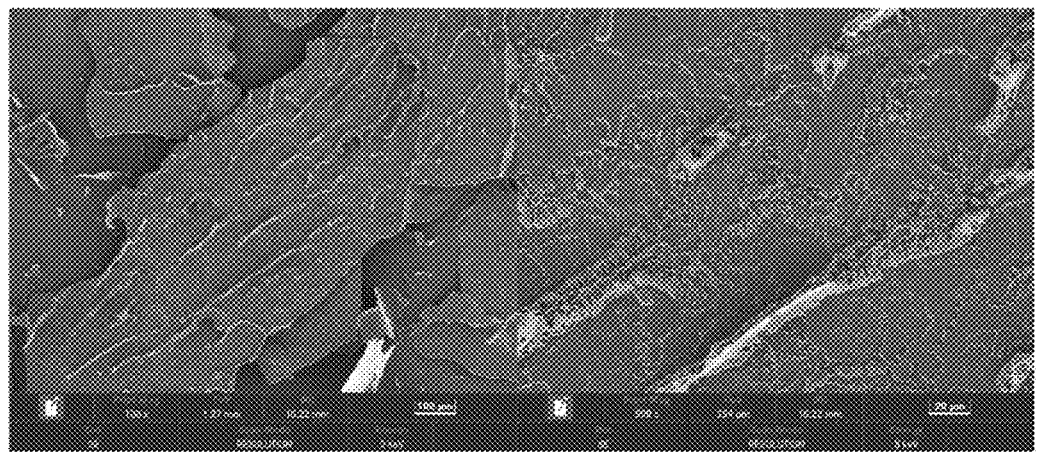
FIG. 7 is a scanning electron microscopy photograph of *Lactarius hatsudake* Tanaka polysaccharide LHP-5.

(1) Molecular weight analysis: 1 mg of the *Lactarius hatsudake* Tanaka polysaccharides LHP-1/2/3/4/5 were formulated with dextran standard to 0.1 mg/mL solution, the resultant was analyzed by a gel chromatograph, and molecular weights of *Lactarius hatsudake* Tanaka refined polysaccharide LHP and LHP-1/2/3/4/5 were tested. Experimental results are as shown in FIG. 2, where weight-average molecular weights of the *Lactarius hatsudake* Tanaka polysaccharides LHP-1/2/3/4/5 are 712 kDa, 515 kDa, 303 kDa, 20 kDa, and 7 kDa respectively.

(2) Scanning electron microscope: the *Lactarius hatsudake* Tanaka polysaccharides LHP-1/2/3/4/5 were immobilized on an aluminum plate with conductive paste, gold was sprayed under vacuum using an ion sputter coater. Surface morphology of each sample was analyzed by scanning electron microscope, and results are as shown in FIG. 3, FIG. 4, FIG. 5, FIG. 6, and FIG. 7 (respectively corresponding to the *Lactarius hatsudake* Tanaka polysaccharides LHP-1/2/3/4/5).

Figure 8:
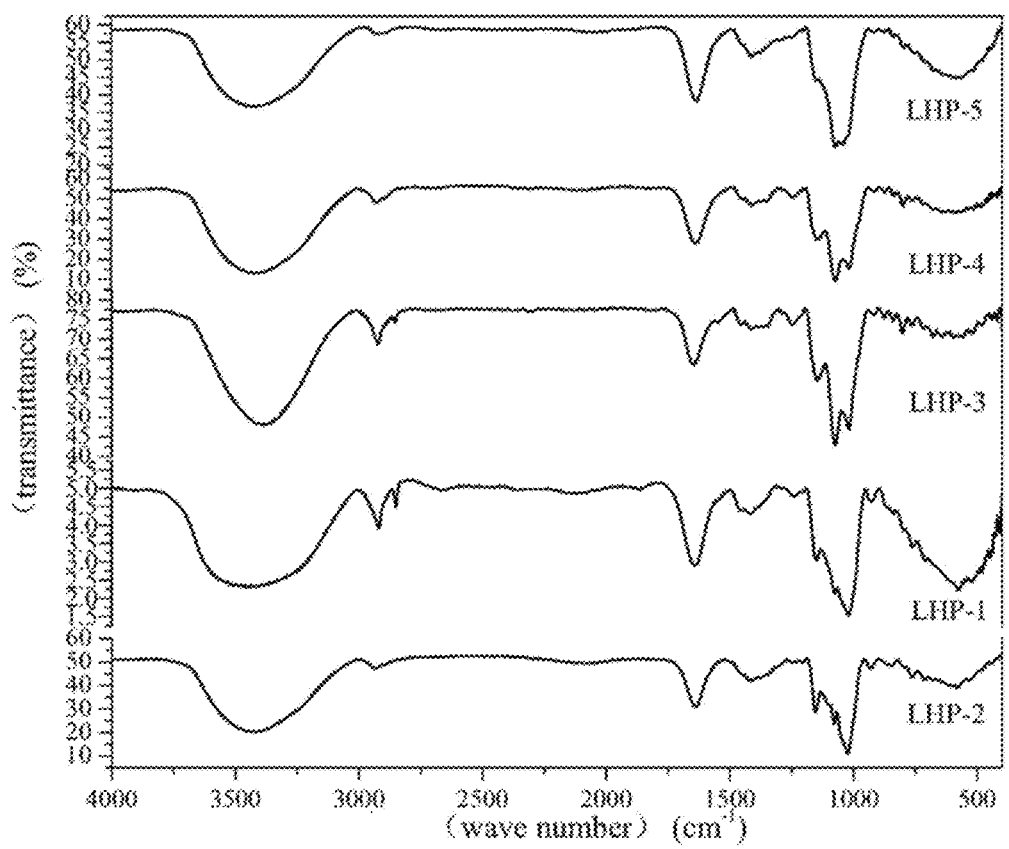
FIG. 8 is an infrared spectrogram of *Lactarius hatsudake* Tanaka polysaccharides LHP-1/2/3/4/5.

(3) Infrared spectrum: 1 mg of the *Lactarius hatsudake* Tanaka polysaccharides LHP-1/2/3/4/5 freeze-dried samples were uniformly mixed with 100 mg of KBr solid, the mixture was ground into powder, then the powder was pressed into a 1 mm thick disc to form a transparent tablet, and the transparent tablet was scanned by a Fourier transform infrared spectrometer in a frequency range of 4000-400 $cm^{-1}$, as shown in FIG. 8.

(4) Monosaccharide composition: a certain amount of sample (about 2 mg) was weighed into a 1.5 mL EP tube, and a 4 mg/mL sample solution was formulated. 200 μL of the sample solution was taken into a test tube with a plug, 400 μL of a 4M trifluoroacetic acid solution was added to mix well, the mixture was hydrolyzed for 2 h under an oil bath condition of 110° C., and subsequently blown dry with nitrogen, and then 400 μL of ethanol was added to dissolve the same. To the monosaccharide sample, ultrapure water was added to formulate a 1 mg/mL solution for later use. 100 μL of the above solution (monosaccharide solution or polysaccharide hydrolysate) was taken into a 2 mL EP tube, 100 μL of a 0.3 M NaOH solution and 0.5 M PMP-methanol solution were respectively added, after they were well mixed, the mixture reacted at 70° C. for 30 min, and after cooling, 0.3 M HCl solution was added, the resultant was supplemented with water to 1 mL, and then 1 mL of trichloromethane was added to extract PMP, and the above operations were repeated for three times. Upper-layer solution was filtered with a film for later use.

LHPLC condition: a chromatography column was Sepax Bio-C18, 4.6×250 mm, 5 μm, a detector was SPD-20A Ultraviolet Detector, a wavelength was 250 nm, a mobile phase was 0.05 M ammonium formate solution and acetonitrile, at a ratio of 83:17, and a flow rate was 1 mL/min.

Figure 9:
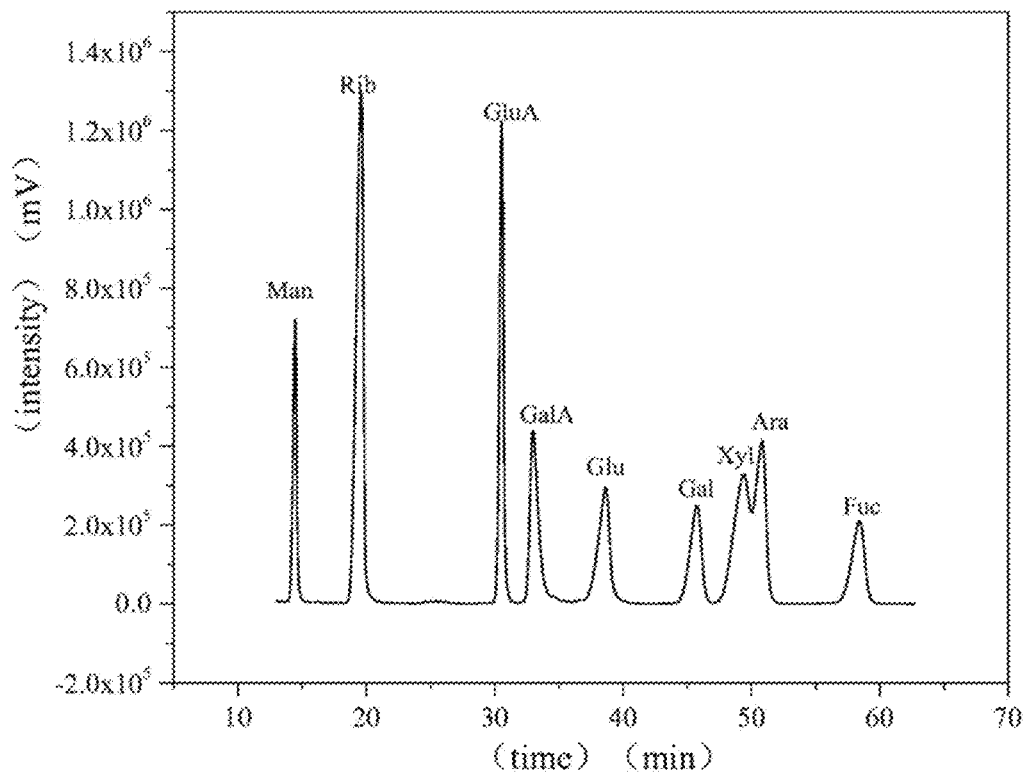
FIG. 9 shows a standard substance elution curve.
Figure 10:
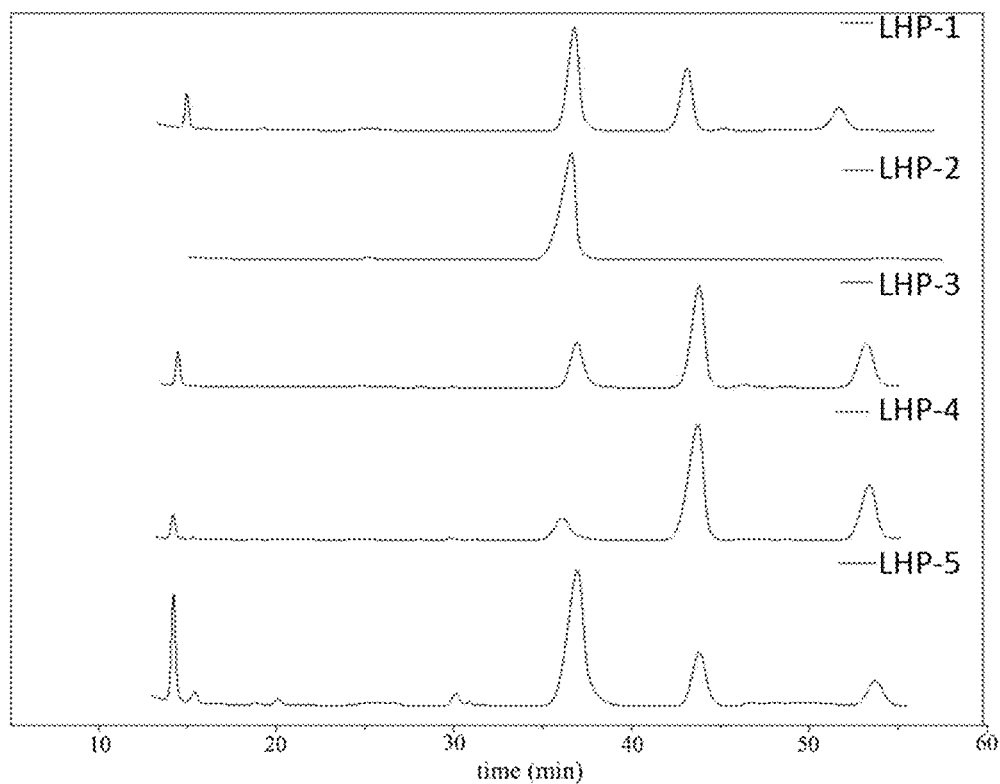
FIG. 10 is sample scan curve of *Lactarius hatsudake* Tanaka polysaccharides LHP-1/2/3/4/5.
Figure 11:
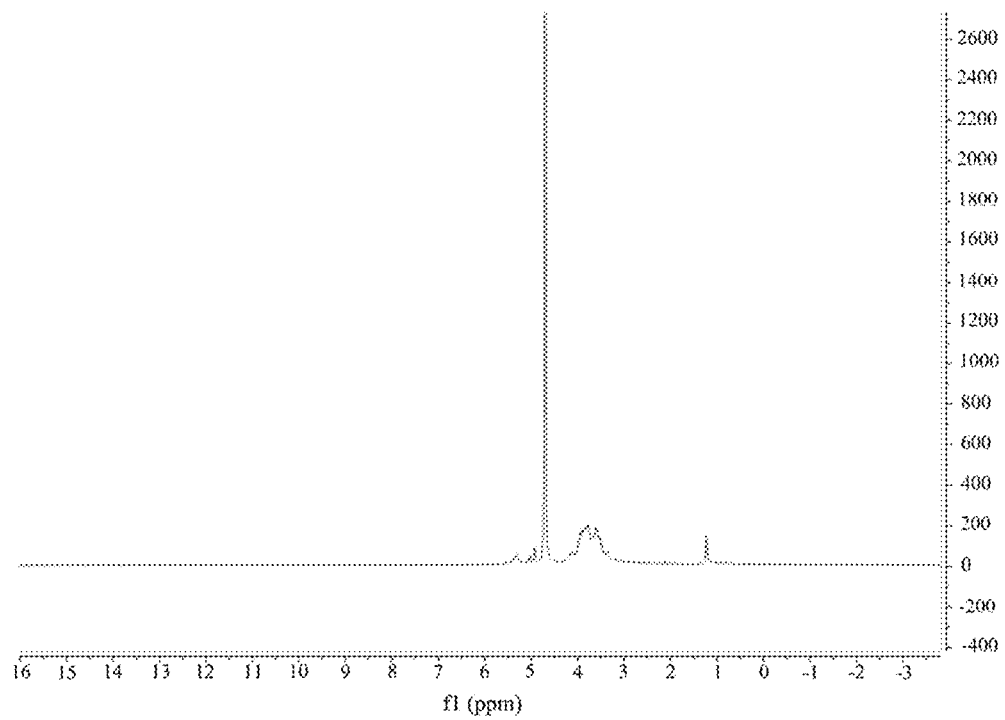
FIG. 11 is a $^1$H-NMR spectrogram of the *Lactarius hatsudake* Tanaka polysaccharide LHP-1.
Figure 12:
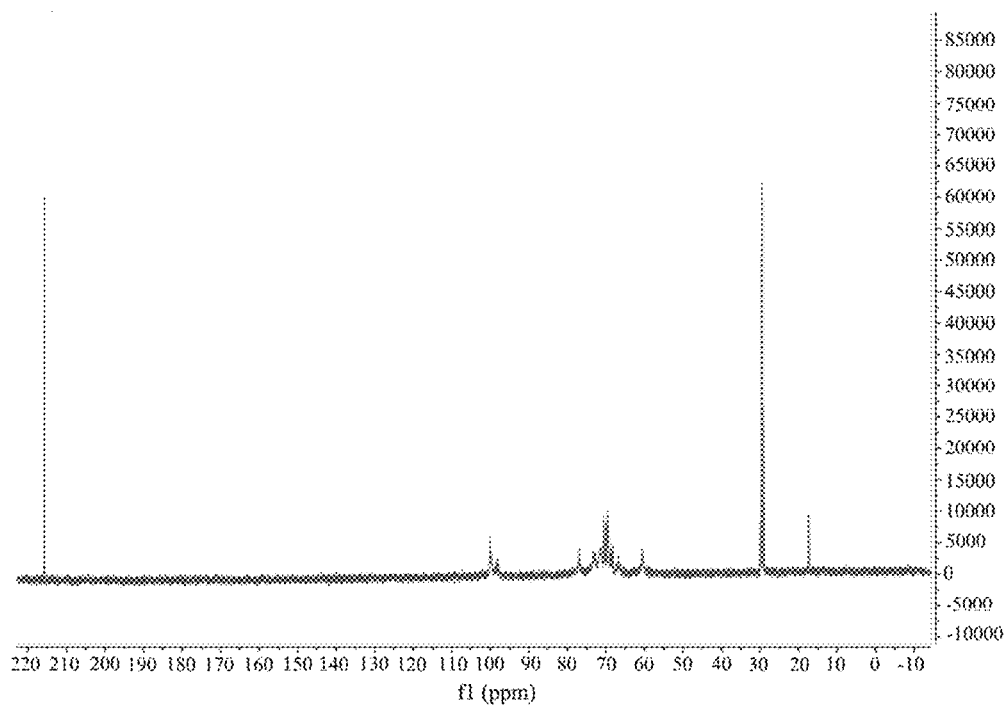
FIG. 12 is a $^{13}$C-NMR spectrogram of the *Lactarius hatsudake* Tanaka polysaccharide LHP-1.
Figure 13:
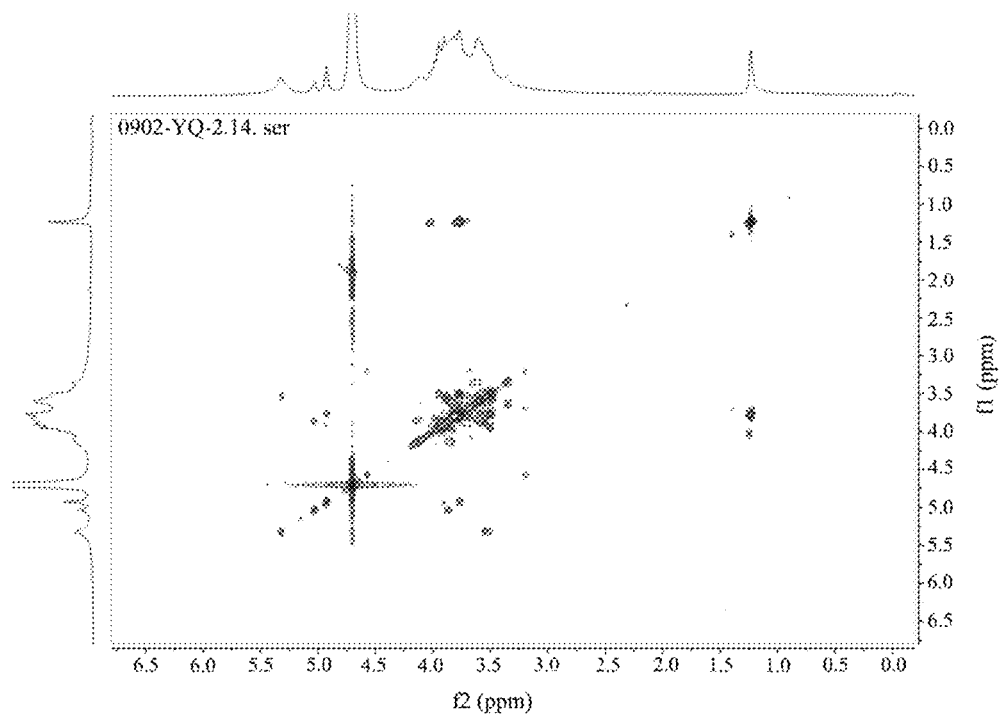
FIG. 13 is a $^1$H-$^1$H-COSY spectrogram of the *Lactarius hatsudake* Tanaka polysaccharide LHP-1.
Figure 14:
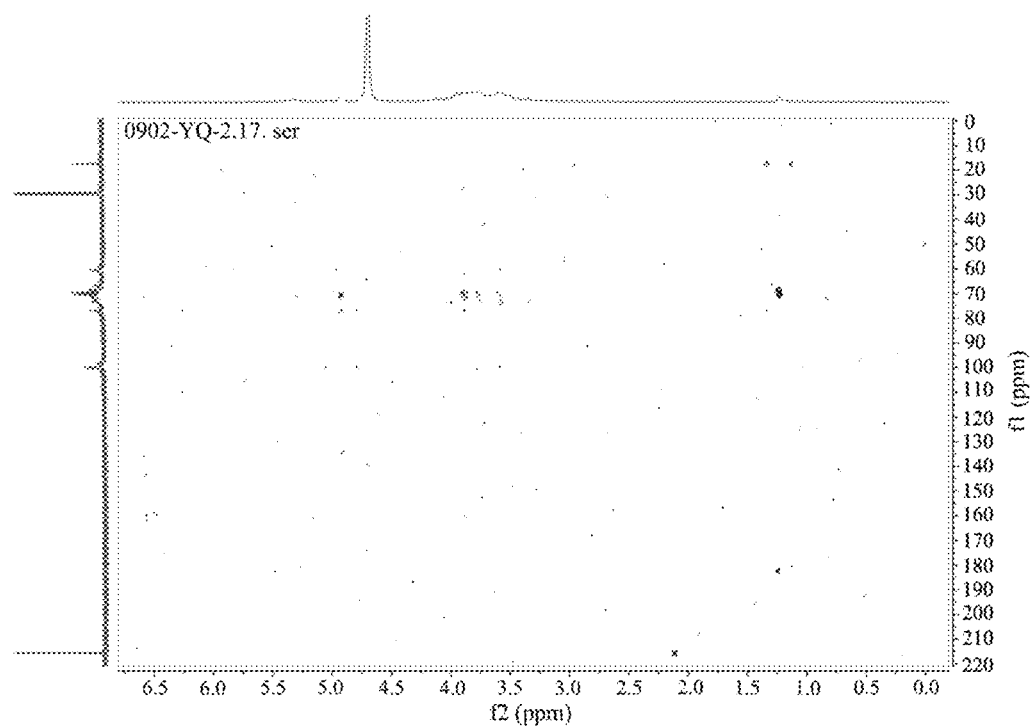
FIG. 14 is an HMBC spectrogram of the *Lactarius hatsudake* Tanaka polysaccharide LHP-1.
Figure 15:
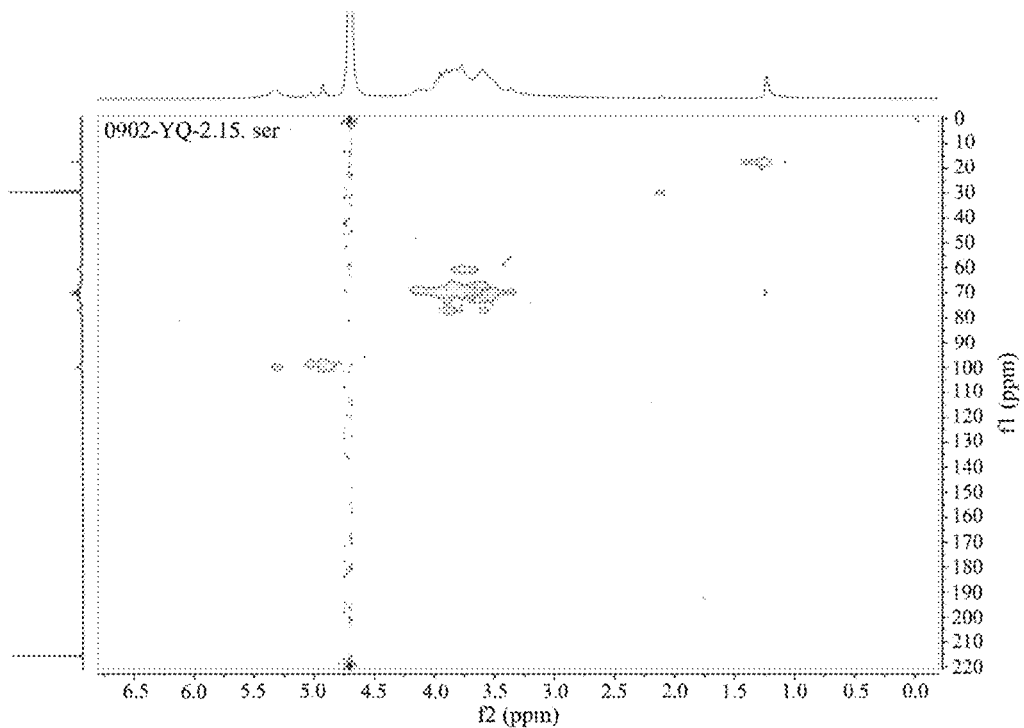
FIG. 15 is an HSQC spectrogram of the *Lactarius hatsudake* Tanaka polysaccharide LHP-1.
Figure 16:
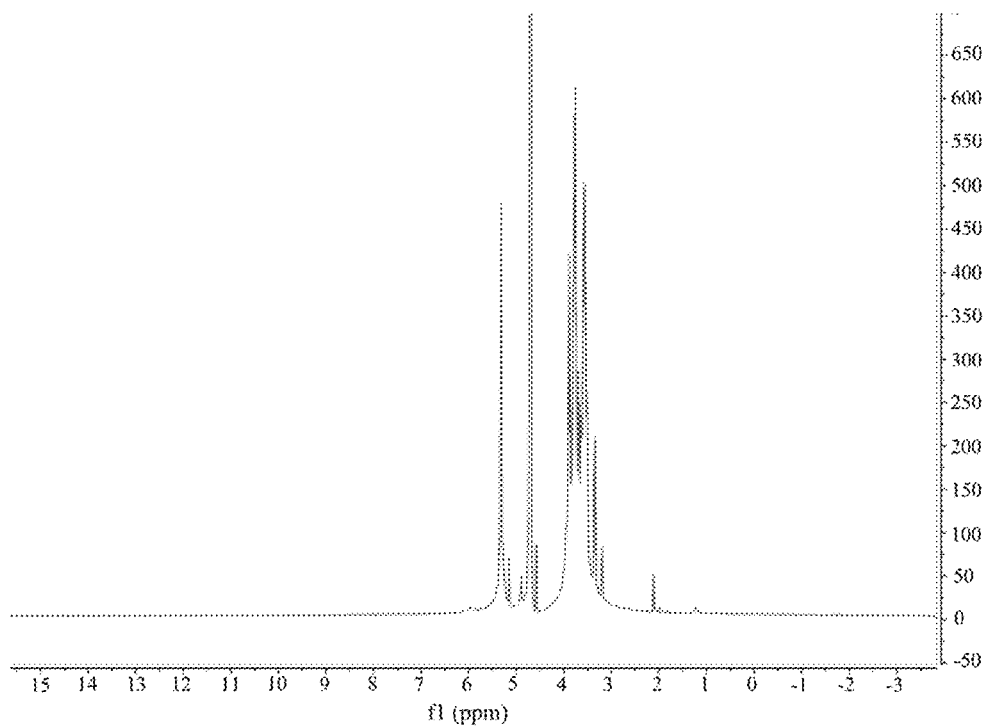
FIG. 16 is a $^1$H-NMR spectrogram of the *Lactarius hatsudake* Tanaka polysaccharide LHP-2.
Figure 17:
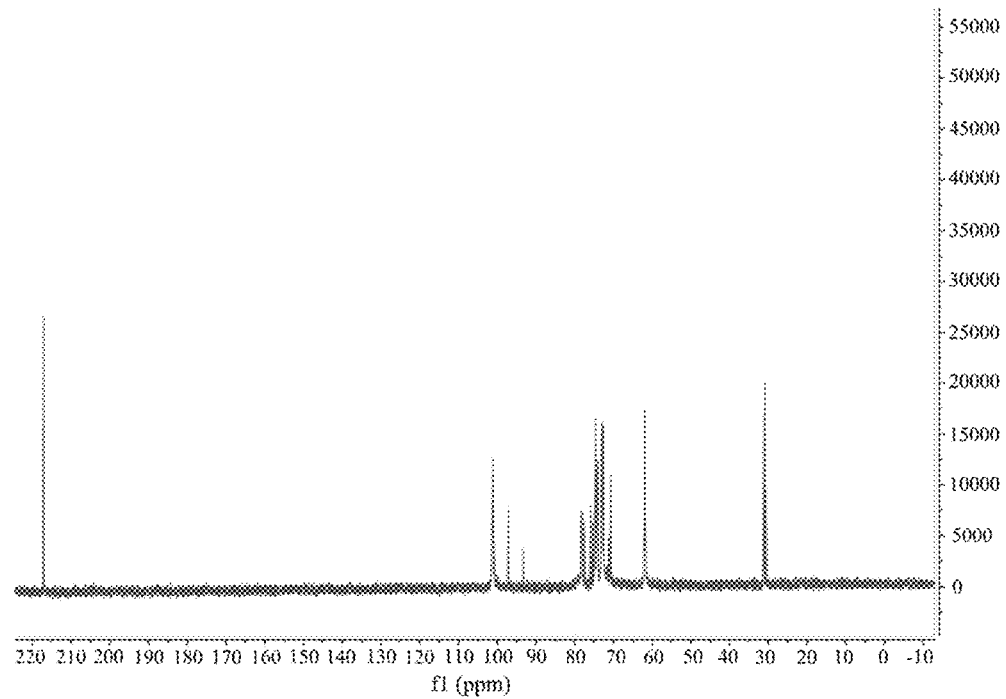
FIG. 17 is a $^{13}$C-NMR spectrogram of the *Lactarius hatsudake* Tanaka polysaccharide LHP-2.
Figure 18:
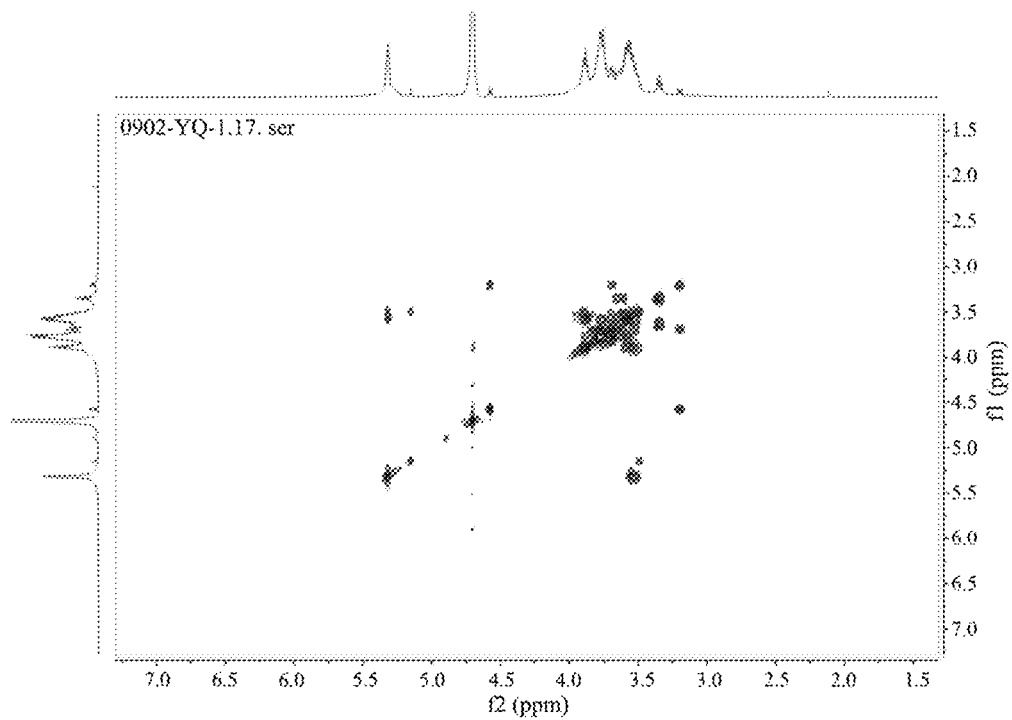
FIG. 18 is a $^1$H-$^1$H-COSY spectrogram of the *Lactarius hatsudake* Tanaka polysaccharide LHP-2.
Figure 19:
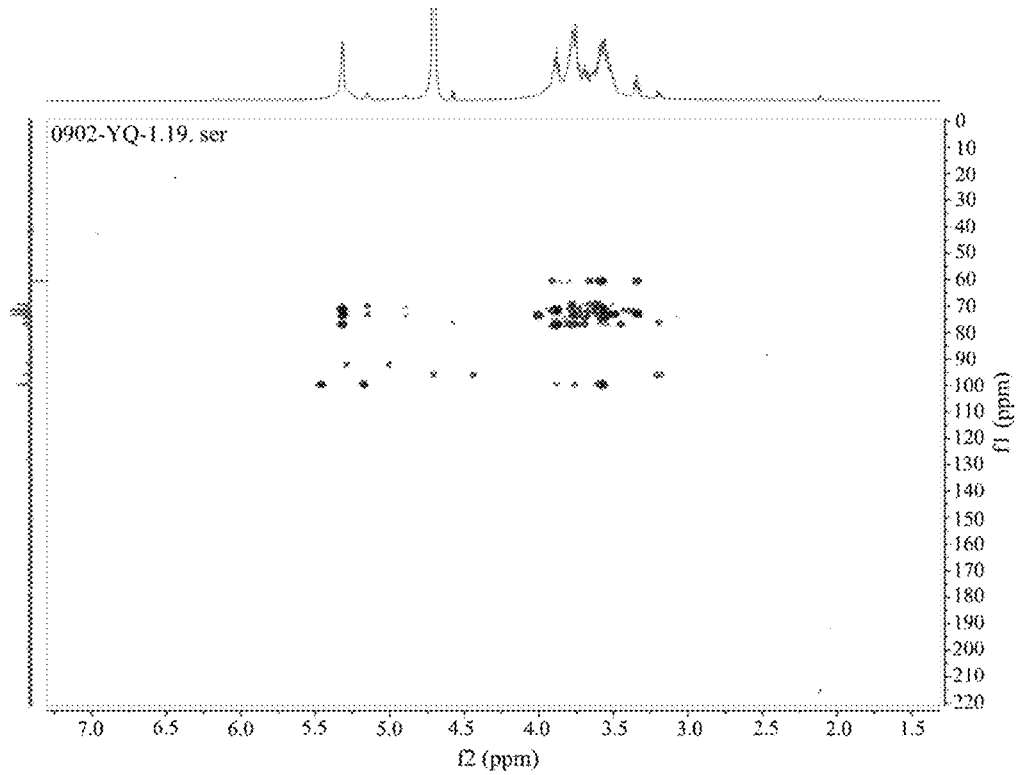
FIG. 19 is an HMBC spectrogram of the *Lactarius hatsudake* Tanaka polysaccharide LHP-2.
Figure 20:
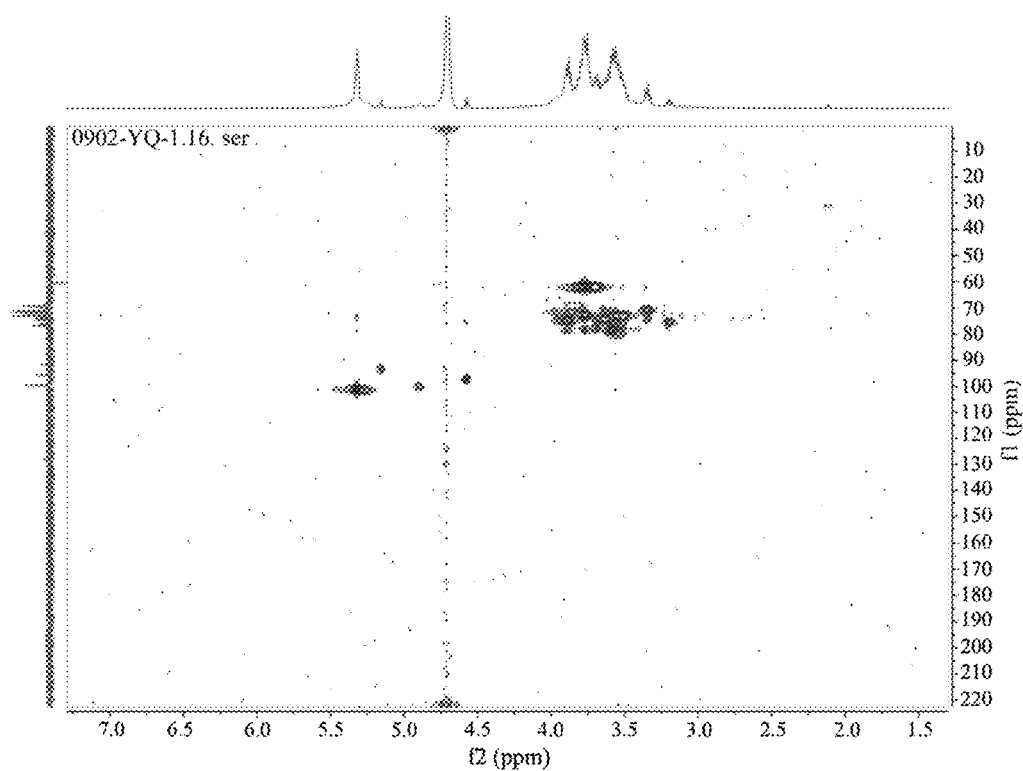
FIG. 20 is an HSQC spectrogram of the *Lactarius hatsudake* Tanaka polysaccharide LHP-2.
Figure 21:
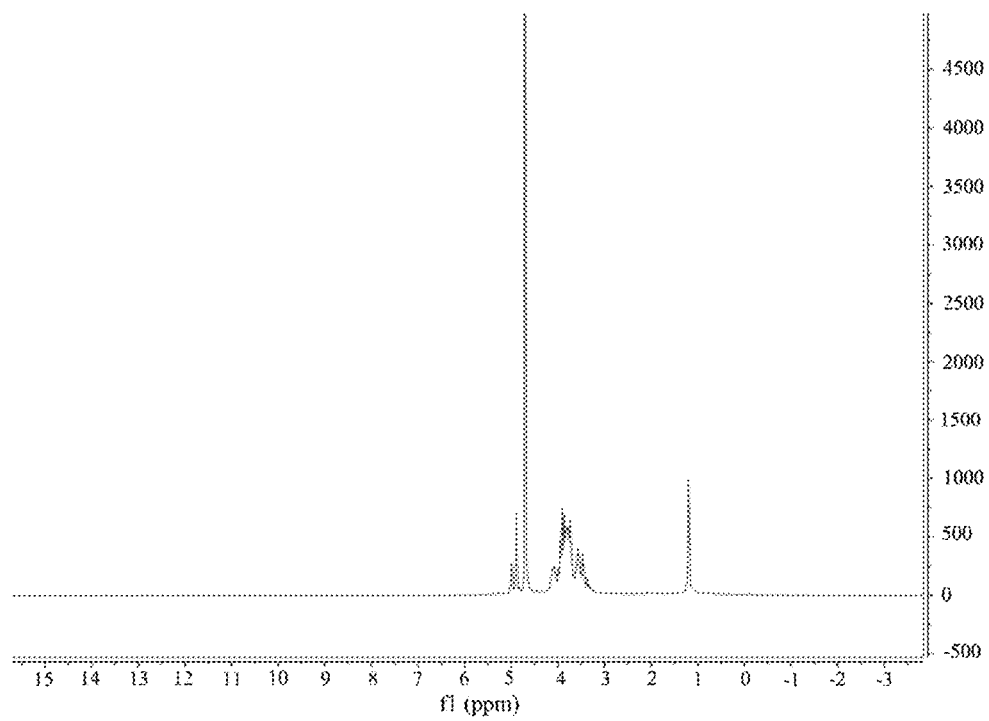
FIG. 21 is a $^1$H-NMR spectrogram of the *Lactarius hatsudake* Tanaka polysaccharide LHP-3.
Figure 22:
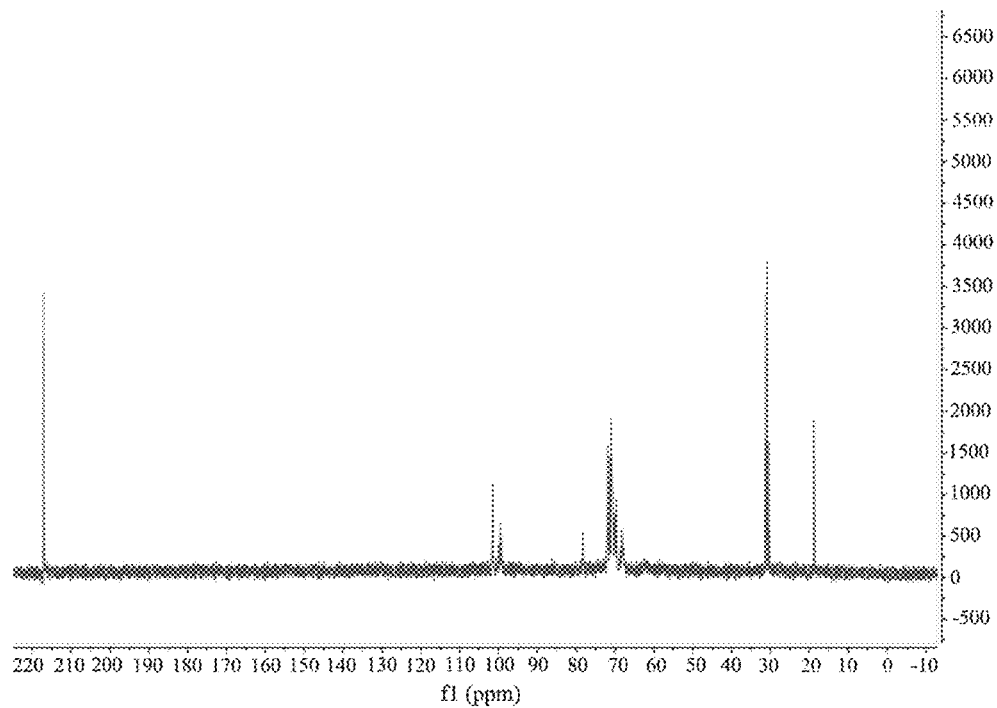
FIG. 22 is a $^{13}$C-NMR spectrogram of the *Lactarius hatsudake* Tanaka polysaccharide LHP-3.
Figure 23:
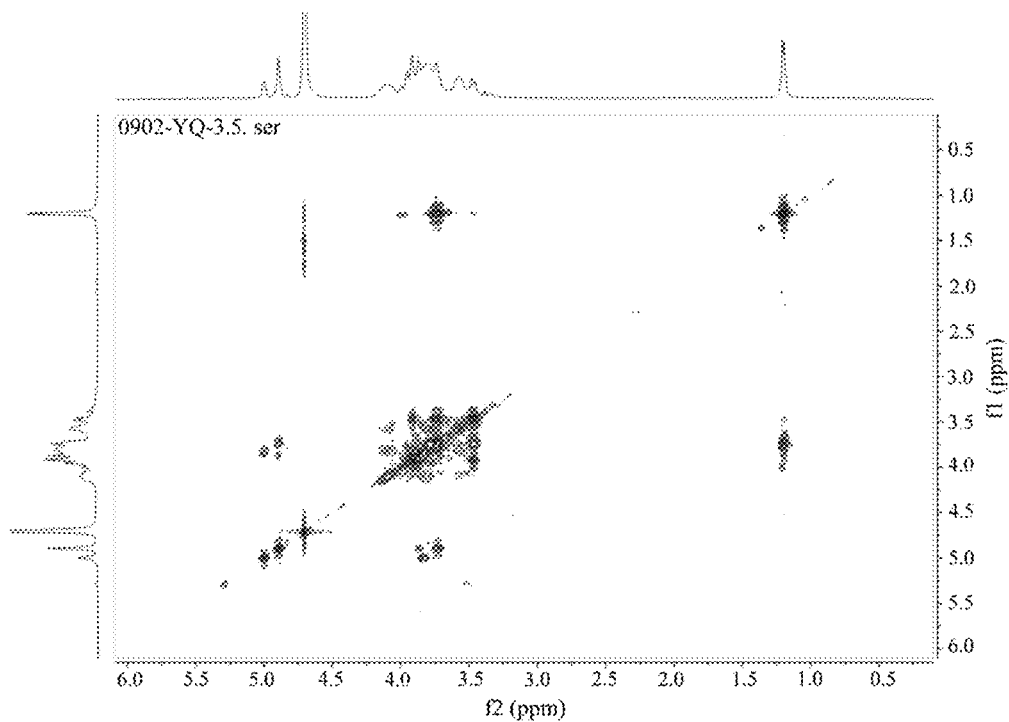
FIG. 23 is a $^1$H-$^1$H-COSY spectrogram of the *Lactarius hatsudake* Tanaka polysaccharide LHP-3.
Figure 24:
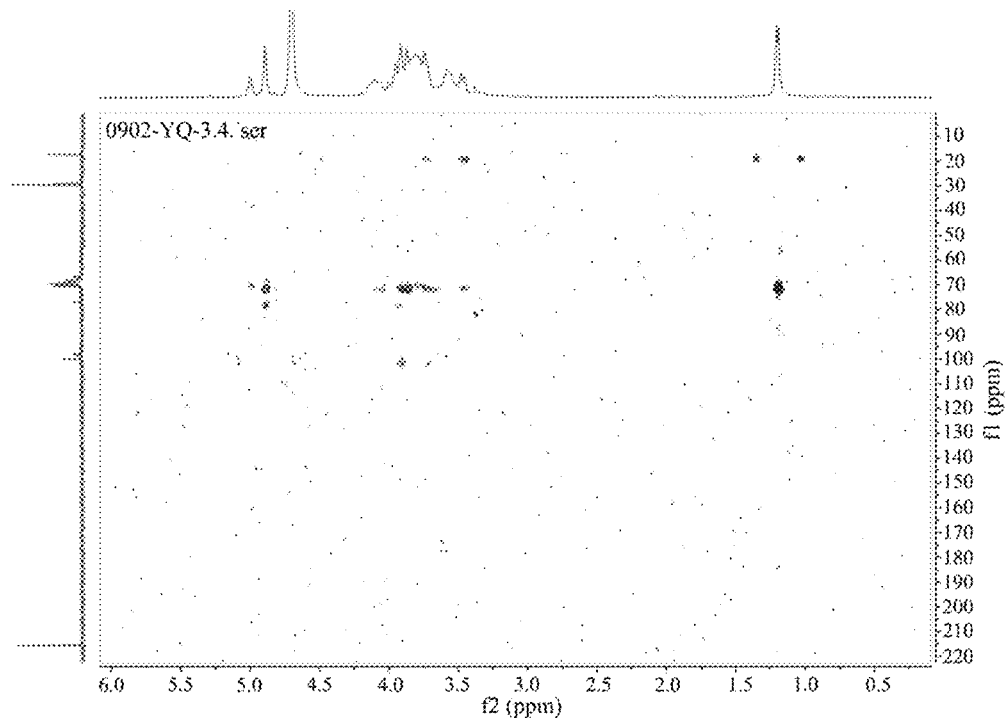
FIG. 24 is an HMBC spectrogram of the *Lactarius hatsudake* Tanaka polysaccharide LHP-3.
Figure 25:
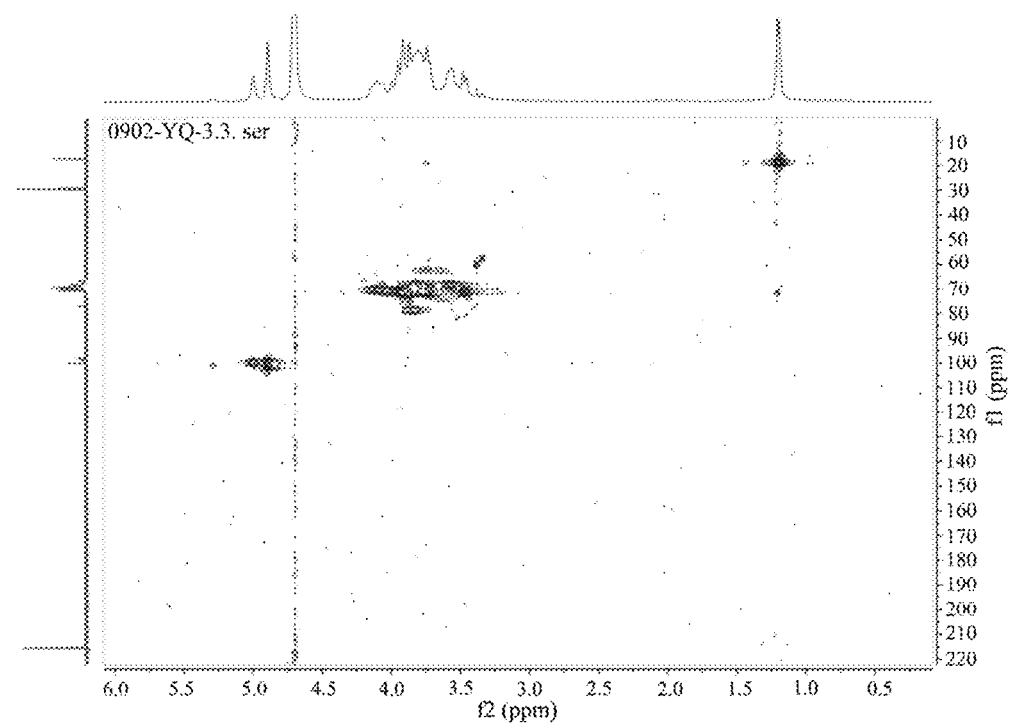
FIG. 25 is an HSQC spectrogram of the *Lactarius hatsudake* Tanaka polysaccharide LHP-3.
Figure 26:
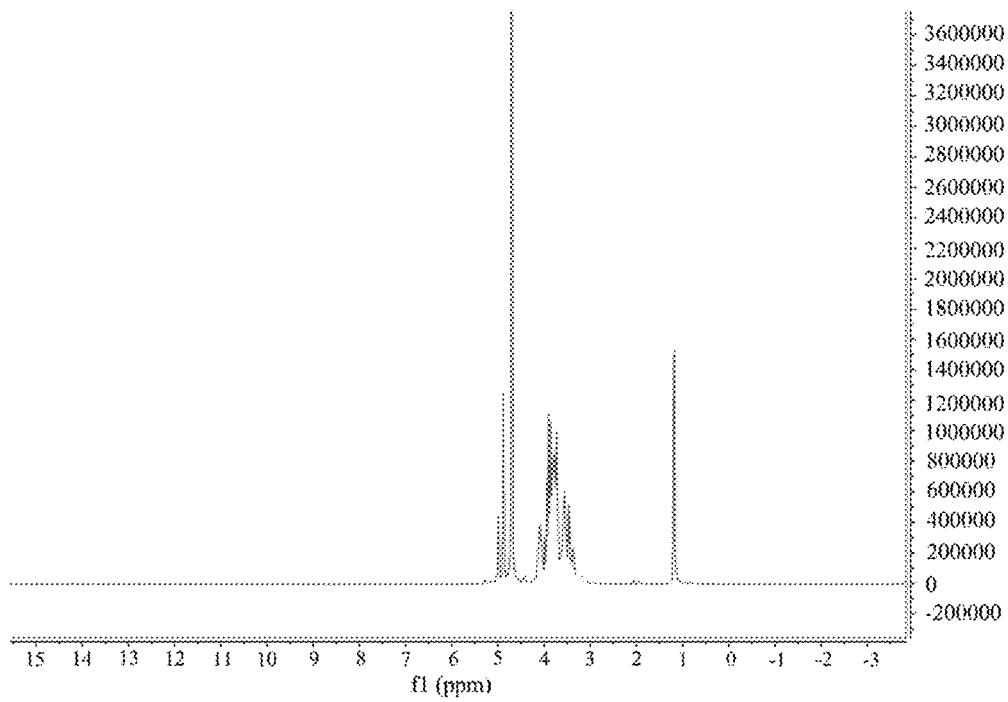
FIG. 26 is a $^1$H-NMR spectrogram of the *Lactarius hatsudake* Tanaka polysaccharide LHP-4.
Figure 27:
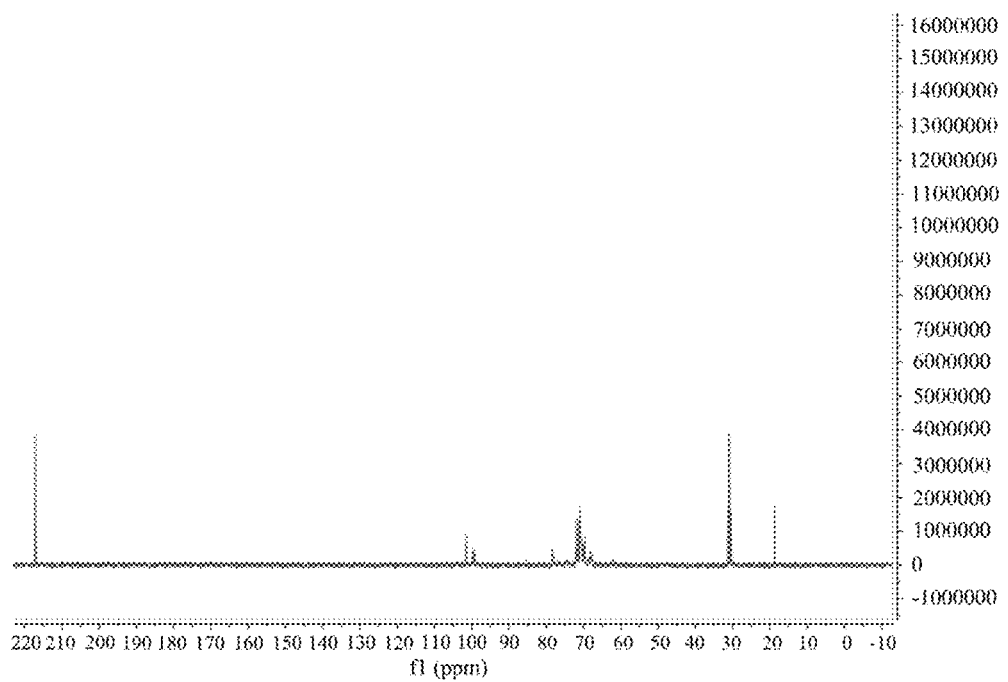
FIG. 27 is a $^{13}$C-NMR spectrogram of the *Lactarius hatsudake* Tanaka polysaccharide LHP-4.
Figure 28:
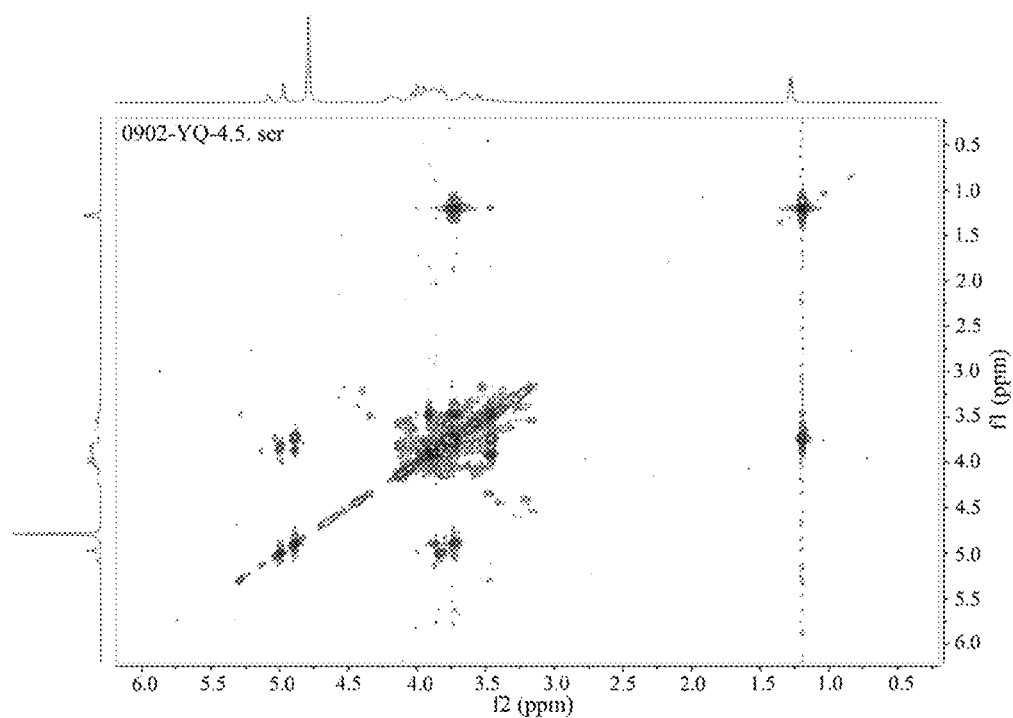
FIG. 28 is a $^1$H-$^1$H-COSY spectrogram of the *Lactarius hatsudake* Tanaka polysaccharide LHP-4.
Figure 29:
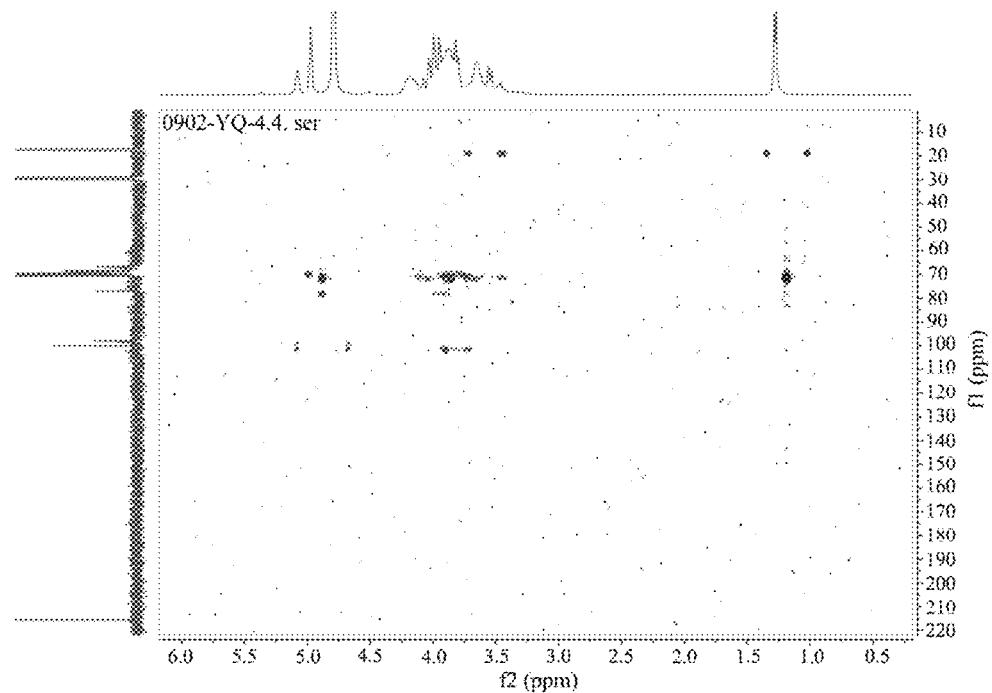
FIG. 29 is an HMBC spectrogram of the *Lactarius hatsudake* Tanaka polysaccharide LHP-4.
Figure 30:
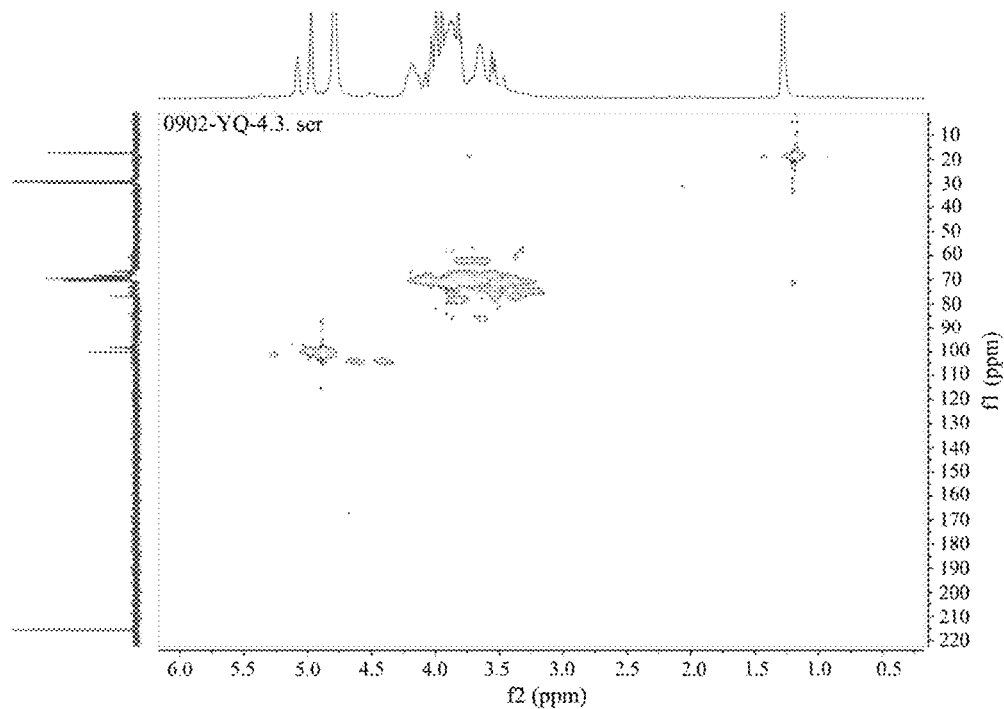
FIG. 30 is an HSQC spectrogram of the *Lactarius hatsudake* Tanaka polysaccharide LHP-4.
Figure 31:
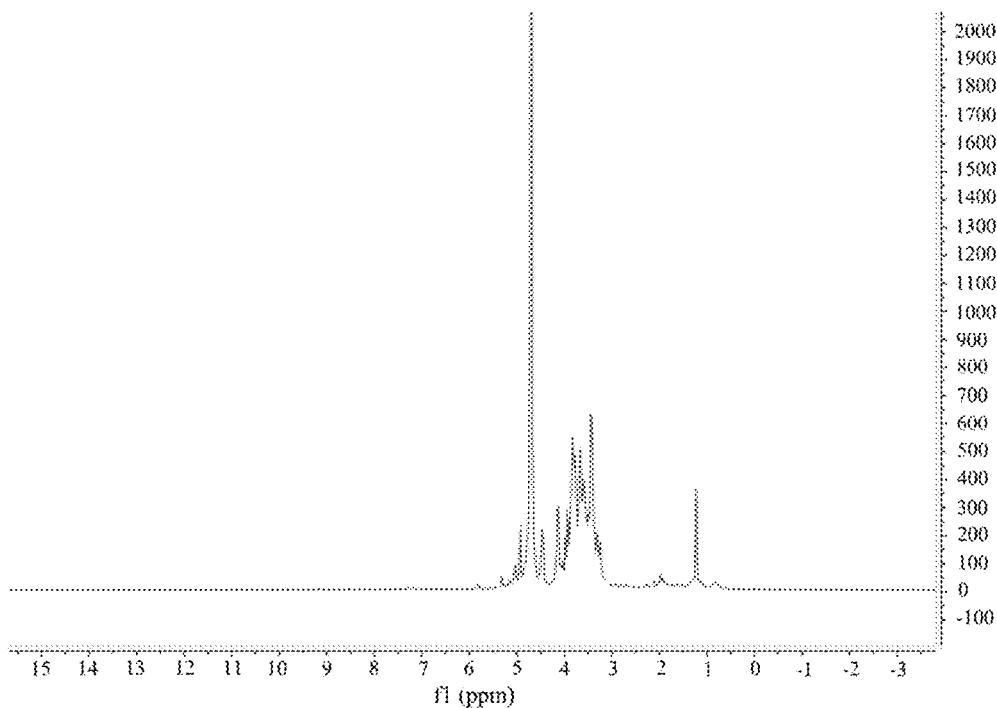
FIG. 31 is a $^1$H-NMR spectrogram of the *Lactarius hatsudake* Tanaka polysaccharide LHP-5.
Figure 32:
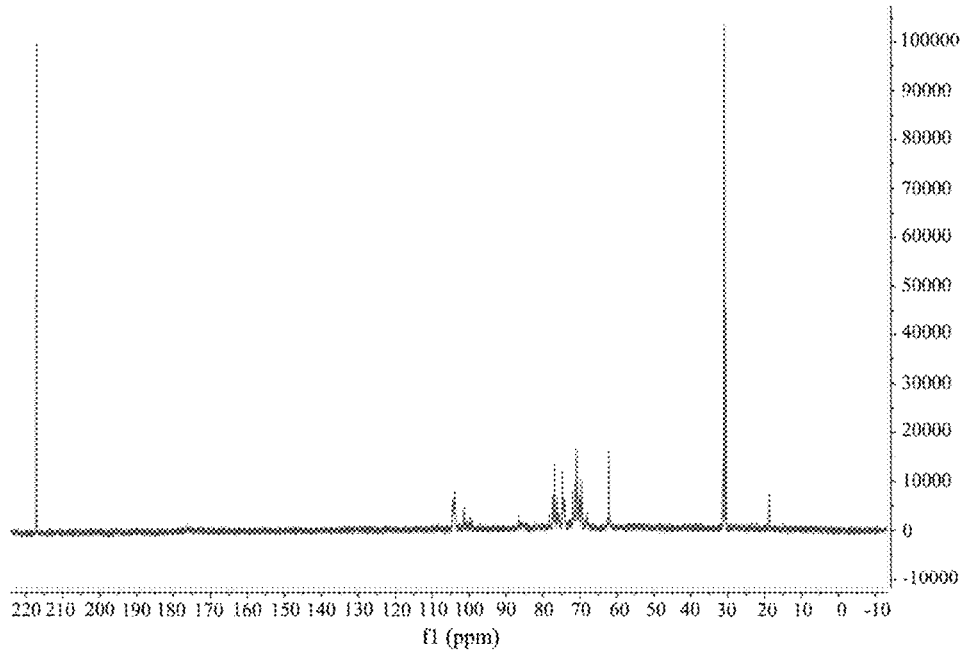
FIG. 32 is a $^{13}$C-NMR spectrogram of the *Lactarius hatsudake* Tanaka polysaccharide LHP-5.
Figure 33:
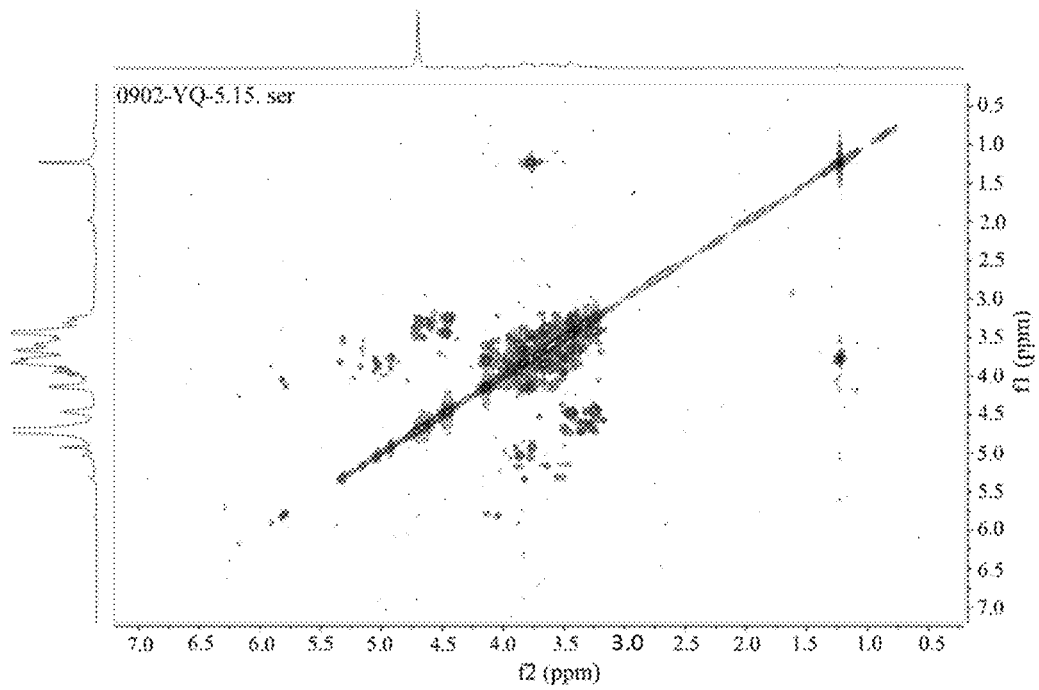
FIG. 33 is a $^1$H-$^1$H-COSY spectrogram of the *Lactarius hatsudake* Tanaka polysaccharide LHP-5.
Figure 34:
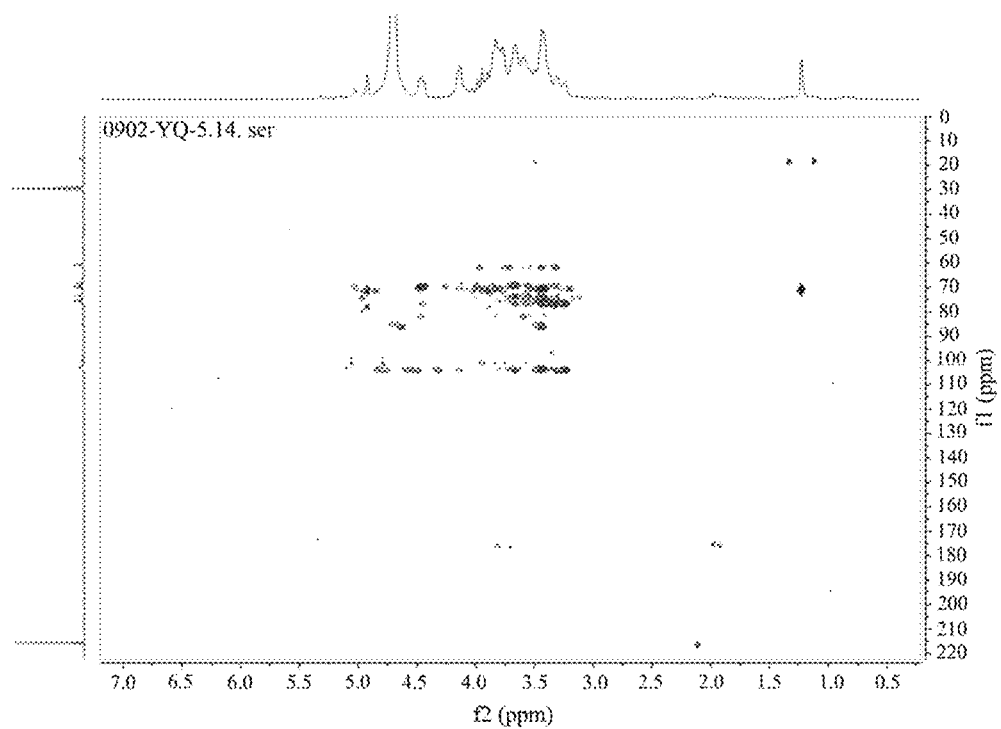
FIG. 34 is an HMBC spectrogram of the *Lactarius hatsudake* Tanaka polysaccharide LHP-5.
Figure 35:
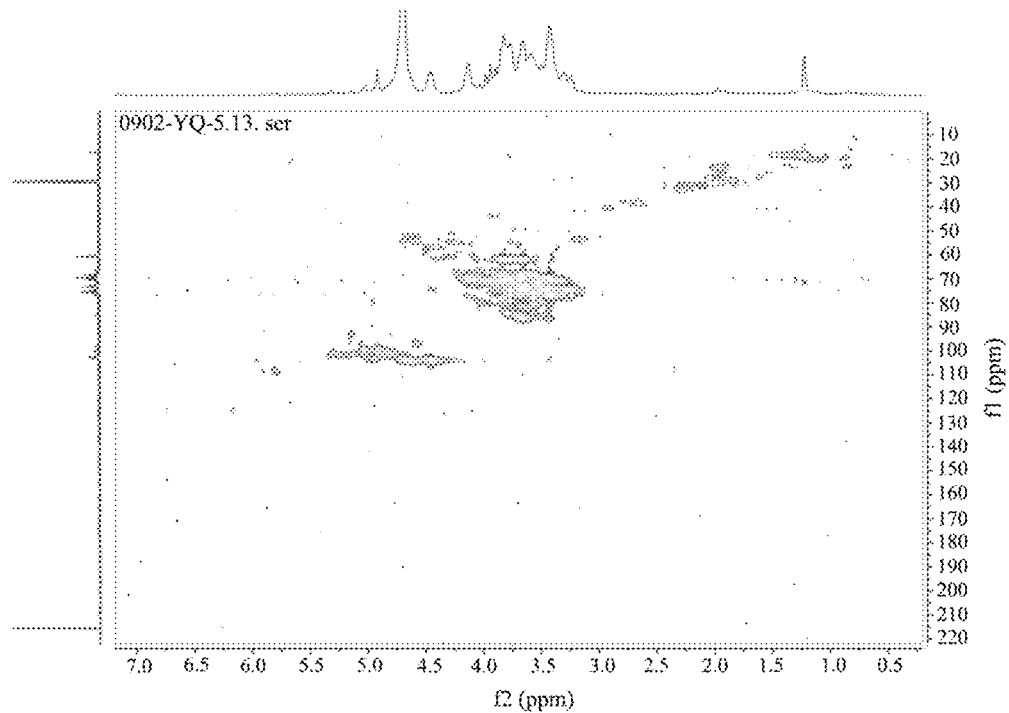
FIG. 35 is an HSQC spectrogram of the *Lactarius hatsudake* Tanaka polysaccharide LHP-5.

An elution curve obtained with standard substances, which are mannose, ribose, glucuronic acid, galacturonic acid, glucose, galactose, xylose, arabinose, and fucose in sequence, is as shown in FIG. 9, and a sample scan diagram is as shown in FIG. 10.

(5) Methylation analysis for *Lactarius hatsudake* Tanaka polysaccharides LHP-1/2/3/4/5:
the polysaccharide sample (2-3 mg) was weighed and placed into a glass reaction bottle, 1 mL of anhydrous DMSO was added, a solution of methylation reagent A was rapidly added, the mixture was sealed, and dissolved under the action of ultrasound, and then a solution of methylation reagent B was added. Reaction was carried out for 60 min in a 30° C. water bath under magnetic stirring. Finally, 2 mL of ultrapure water was added to the above mixture to terminate methylation reaction.

Methylated polysaccharide was added with 1 mL of 2 M trifluoroacetic acid (TFA) for hydrolysis for 90 min, followed by evaporation to dryness through a rotary evaporator. To residue, 2 mL of double distilled water and 60 mg of sodium borohydride were added for reduction for 8 h, glacial acetic acid was added for neutralization, the mixture was subjected to rotary evaporation, and drying at 101° C. oven, then 1 mL of acetic anhydride was added for acetylation reaction at 100° C. for 1 h, and the resultant was cooled. Then 3 mL of toluene was added, followed by concentrating under reduced pressure and evaporation to dryness. The operations were repeated for 4-5 times, to remove excess acetic anhydride.

A product after the acetylation was dissolved in 3 mL of $CH_2Cl_2$, and then transferred to a separating funnel, a small amount of distilled water was added, after thorough shaking, an upper-layer aqueous solution was removed. Such operations were repeated for 4 times. $CH_2Cl_2$ layer was dried with an appropriate amount of anhydrous sodium sulfate to a volume of 10 mL, and the resultant was placed into a liquid phase vial. Analysis was performed by Shimadzu GCMS-QP 2010 gas chromatograph-mass spectrometer to measure an acetylated product sample.

GC-MS condition: RXI-5SIL MS chromatography column was 30 m*0.25 mm*0.25 μm; program heating condition was: start temperature was 120° C., and the temperature was raised to 250° C. at 3° C./min and held for 5 min; a sample inlet temperature was 250° C., a detector temperature was 250° C., a carrier gas was helium, and a flow rate was 1 mL/min. Results are as shown in Table 1, Table 2, Table 3, Table 4, and Table 5.

TABLE 1

Analysis of Results of Polysaccharide Methylated Sugar Alcohol Acetyl Ester (PMAA) of LHP-1 Purified Component

| RT | Methylated sugar | Mass fragments (m/z) | Molar ratio | Type of linkage |
|---|---|---|---|---|
| 17.629 | 2,3,5-Me3-Xylp | 43, 71, 87, 101, 117, 129, 145, 161 | 0.008 | Xylp-(1→ |
| 17.953 | 2,3,4-Me3-Fucp | 43, 59, 72, 89, 101, 115, 117, 131, 175 | 0.087 | Fucp-(1→ |
| 21.394 | 2,4-Me2-Xylp | 43, 58, 85, 99, 101, 117, 127, 159, 173 | 0.005 | →3)-Xylp-(1→ |
| 21.718 | 2,3-Me2-Xylp | 43, 71, 87, 99, 101, 117, 129, 161, 189 | 0.004 | →4)-Xylp-(1→ |
| 23.766 | 2,3,4,6-Me4-Glcp | 43, 71, 87, 101, 117, 129, 145, 161, 205 | 0.051 | Glcp-(1→ |
| 24.685 | 2,3,4,6-Me4-Galp | 43, 71, 87, 101, 117, 129, 145, 161, 205 | 0.007 | Galp-(1→ |
| 29.994 | 2,3,6-Me3-Glcp | 43, 87, 99, 101, 113, 117, 129, 131, 161, 173, 233 | 0.554 | →4)-Glcp-(1→ |
| 30.705 | 2,3,4-Me3-Glcp | 43, 87, 99, 101, 117, 129, 161, 189, 233 | 0.003 | →6-Glcp-(1→ |
| 32.709 | 2,3,4-Me3-Galp | 43, 87, 99, 101, 117, 129, 161, 189, 233 | 0.069 | →6)-Galp-(1→ |
| 33.465 | 2,6-Me2-Glcp | 43, 87, 97, 117, 159, 185 | 0.029 | →3,4)-Glcp-(1→ |
| 36.483 | 2,3-Me2-Glcp | 43, 71, 85, 87, 99, 101, 117, 127, 159, 161, 201 | 0.068 | →4,6)-Glcp-(1→ |

TABLE 2

Analysis of Results of Polysaccharide Methylated Sugar Alcohol Acetyl Ester (PMAA) of LHP-2 Purified Component

| 38.665 | 3,4-Me2-Manp | 43, 87, 99, 129, 189 | 0.117 | →2,6)-Manp-(1→ |
|---|---|---|---|---|
| 40.748 | 2-Me1-Glcp | 43, 58, 87, 97, 117, 139 | 0.006 | →3,4,6)-Glcp-(1→ |

TABLE 3

Analysis of Results of Polysaccharide Methylated Sugar Alcohol Acetyl Ester (PMAA) of LHP-3 Purified Component

| RT | Methylated sugar | Mass fragments (m/z) | Molar ratio | Type of linkage |
|---|---|---|---|---|
| 17.959 | 2,3,4-Me3-Fucp | 43, 59, 72, 89, 101, 115, 117, 131, 175 | 0.007 | Fucp-(1→ |
| 23.889 | 2,3,4,6-Me4-Glcp | 43, 71, 87, 101, 117, 129, 145, 161, 205 | 0.056 | Glcp-(1→ |
| 29.1 | 2,3,6-Me3-Galp | 43, 87, 99, 101, 113, 117, 129, 131, 161, 173, 233 | 0.014 | →4)-Galp-(1→ |
| 30.404 | 2,3,6-Me3-Glcp | 43, 87, 99, 101, 113, 117, 129, 131, 161, 173, 233 | 0.790 | →4)-Glcp-(1→ |
| 33.619 | 2,6-Me2-Glcp | 43, 87, 97, 117, 159, 185 | 0.046 | →3,4)-Glcp-(1→ |
| 36.661 | 2,3-Me2-Glcp | 43, 71, 85, 87, 99, 101, 117, 127, 159, 161, 201 | 0.081 | →4,6)-Glcp-(1→ |
| 40.815 | 2-Me1-Glcp | 43, 58, 87, 97, 117, 139 | 0.006 | →3,4,6)-Glcp-(1→ |

TABLE 4

Analysis of Results of Polysaccharide Methylated Sugar Alcohol Acetyl Ester (PMAA) of LHP-4 Purified Component

| RT | Methylated sugar | Mass fragments (m/z) | Molar ratio | Type of linkage |
|---|---|---|---|---|
| 17.623 | 2,3,5-Me3-Xylp | 43, 71, 87, 101, 117, 129, 145, 161 | 0.008 | Xylp-(1→ |
| 18.047 | 2,3,4-Me3-Fucp | 43, 59, 72, 89, 101, 115, 117, 131, 175 | 0.136 | Fucp-(1→ |
| 21.398 | 2,4-Me2-Xylp | 43, 58, 85, 99, 101, 117, 127, 159, 173 | 0.007 | →3)-Xylp-(1→ |
| 21.727 | 2,3-Me2-Xylp | 43, 71, 87, 99, 101, 117, 129, 161, 189 | 0.005 | →4)-Xylp-(1→ |
| 23.712 | 2,3,4,6-Me4-Glcp | 43, 71, 87, 101, 117, 129, 145, 161, 205 | 0.014 | Glcp-(1→ |
| 24.693 | 2,3,4,6-Me4-Galp | 43, 71, 87, 101, 117, 129, 145, 161, 205 | 0.009 | Galp-(1→ |
| 28.763 | 2,4,6-Me3-Glcp | 43, 87, 99, 101, 117, 129, 161, 173, 233 | 0.022 | →3)-Glcp-(1→ |
| 29.565 | 2,3,6-Me3-Glcp | 43, 87, 99, 101, 113, 117, 129, 131, 161, 173, 233 | 0.070 | →4)-Glcp-(1→ |
| 29.869 | 2,4,6-Me3-Galp | 43, 87, 99, 101, 117, 129, 161, 173, 233 | 0.004 | →3)-Galp-(1→ |
| 30.612 | 2,3,4-Me3-Glcp | 43, 87, 99, 101, 117, 129, 161, 189, 233 | 0.010 | →6-Glcp-(1→ |
| 33.059 | 2,3,4-Me3-Galp | 43, 87, 99, 101, 117, 129, 161, 189, 233 | 0.334 | →6)-Galp-(1→ |
| 33.493 | 2,6-Me2-Glcp | 43, 87, 97, 117, 159, 185 | 0.006 | →3,4)-Glcp-(1→ |
| 36.322 | 2,3-Me2-Glcp | 43, 71, 85, 87, 99, 101, 117, 127, 159, 161, 201 | 0.006 | →3,4)-Glcp-(1→ |
| 36.817 | 2,4-Me2-Galp | 43, 87, 117, 129, 159, 189, 233 | 0.015 | →3,6)-Galp-(1→ |
| 39.17 | 3,4-Me2-Manp | 43, 87, 99, 129, 189 | 0.355 | →2,6)-Manp-(1→ |
| 40.804 | 2-Me1-Galp | 43, 87, 97, 117, 139, 159, 173, 233 | 0.001 | →3,4,6)-Galp-(1→ |

TABLE 5

Analysis of Results of Polysaccharide Methylated Sugar Alcohol Acetyl Ester (PMAA) of LHP-5 Purified Component

| RT | Methylated sugar | Mass fragments (m/z) | Molar ratio | Type of linkage |
|---|---|---|---|---|
| 17.622 | 2,3,5-Me3-Xylp | 43, 71, 87, 101, 117, 129, 145, 161 | 0.010 | Xylp-(1→ |
| 17.993 | 2,3,4-Me3-Fucp | 43, 59, 72, 89, 101, 115, 117, 131, 175 | 0.245 | Fucp-(1→ |
| 21.41 | 2,4-Me2-Xylp | 43, 58, 85, 99, 101, 117, 127, 159, 173 | 0.006 | →3)-Xylp-(1→ |
| 21.705 | 2,3-Me2-Xylp | 43, 71, 87, 99, 101, 117, 129, 161, 189 | 0.002 | →4)-Xylp-(1→ |
| 23.699 | 2,3,4,6-Me4-Glcp | 43, 71, 87, 101, 117, 129, 145, 161, 205 | 0.035 | Glcp-(1→ |
| 24.667 | 2,3,4,6-Me4-Galp | 43, 71, 87, 101, 117, 129, 145, 161, 205 | 0.005 | Galp-(1→ |
| 28.708 | 2,4,6-Me3-Glcp | 43, 87, 99, 101, 117, 129, 161, 173, 233 | 0.013 | →3)-Glcp-(1→ |

TABLE 5-continued

Analysis of Results of Polysaccharide Methylated Sugar Alcohol Acetyl Ester (PMAA) of LHP-5 Purified Component

| RT | Methylated sugar | Mass fragments (m/z) | Molar ratio | Type of linkage |
| --- | --- | --- | --- | --- |
| 29.351 | 2,3,6-Me3-Glcp | 43, 87, 99, 101, 113, 117, 129, 131, 161, 173, 233 | 0.031 | →4)-Glcp-(1→ |
| 30.62 | 2,3,4-Me3-Glcp | 43, 87, 99, 101, 117, 129, 161, 189, 233 | 0.035 | →6-Glcp-(1→ |
| 32.78 | 2,3,4-Me3-Galp | 43, 87, 99, 101, 117, 129, 161, 189, 233 | 0.262 | →6)-Galp-(1→ |
| 33.334 | 2,6-Me2-Glcp | 43, 87, 97, 117, 159, 185 | 0.003 | →3,4)-Glcp-(1→ |
| 36.226 | 2,3-Me2-Glcp | 43, 71, 85, 87, 99, 101, 117, 127, 159, 161, 201 | 0.006 | →4,6)-Glcp-(1→ |
| 36.699 | 2,4-Me2-Galp | 43, 87, 117, 129, 159, 189, 233 | 0.010 | →3,6)-Galp-(1→ |
| 38.702 | 3,4-Me2-Manp | 43, 87, 99, 129, 189 | 0.337 | →2,6)-Manp-(1→ |
| 40.686 | 2-Me1-Galp | 43, 87, 97, 117, 139, 159, 173, 233 | 0.001 | →3,4,6)-Galp-(1→ |

| RT | Methylated sugar | Mass fragments (m/z) | Molar ratio | Type of linkage |
| --- | --- | --- | --- | --- |
| 17.864 | 2,3,4-Me3-Fucp | 43, 59, 72, 89, 101, 115, 117, 131, 175 | 0.018 | Fucp-(1→ |
| 21.403 | 2,4-Me2-Xylp | 43, 58, 85, 99, 101, 117, 127, 159, 173 | 0.002 | →3)-Xylp-(1→ |
| 21.705 | 2,3-Me2-Xylp | 43, 71, 87, 99, 101, 117, 129, 161, 189 | 0.001 | →4)-Xylp-(1→ |
| 23.702 | 2,3,4,6-Me4-Glcp | 43, 71, 87, 101, 117, 129, 145, 161, 205 | 0.069 | Glcp-(1→ |
| 24.646 | 2,3,4,6-Me4-Galp | 43, 71, 87, 101, 117, 129, 145, 161, 205 | 0.002 | Galp-(1→ |
| 26.171 | 2-Me1-Araf | 43, 58, 89, 99, 117, 127, 159, 201 | 0.004 | →3,5)-Araf-(1→ |
| 28.857 | 2,4,6-Me3-Glcp | 43, 87, 99, 101, 117, 129, 161, 173, 233 | 0.351 | →3)-Glcp-(1→ |
| 29.376 | 2,3,6-Me3-Glcp | 43, 87, 99, 101, 113, 117, 129, 131, 161, 173, 233 | 0.059 | →4)-Glcp-(1→ |
| 30.725 | 2,3,4-Me3-Glcp | 43, 87, 99, 101, 117, 129, 161, 189, 233 | 0.150 | →6-Glcp-(1→ |
| 31.999 | 3,6-Me2-D-Glc-2-NAc | 43, 57, 83, 103, 117, 159 | 0.005 | →4)-GlcNAc-(1→ |
| 32.46 | 2,3,4-Me3-Galp | 43, 87, 99, 101, 117, 129, 161, 189, 233 | 0.087 | →6)-Galp-(1→ |
| 33.259 | 2,6-Me2-Glcp | 43, 87, 97, 117, 159, 185 | 0.005 | →3,4)-Glcp-(1→ |
| 36.22 | 2,3-Me2-Glcp | 43, 71, 85, 87, 99, 101, 117, 127, 159, 161, 201 | 0.009 | →4,6)-Glcp-(1→ |
| 36.832 | 2,4-Me2-Glcp | 43, 87, 117, 129, 159, 189, 233 | 0.130 | →3,6)-Glcp-(1→ |
| 37.477 | 2,4-Me2-Galp | 43, 87, 117, 129, 159, 189, 233 | 0.010 | →3,6)-Galp-(1→ |
| 38.374 | 3,4-Me2-Manp | 43, 87, 99, 129, 189 | 0.096 | →2,6)-Manp-(1→ |
| 40.649 | 2-Me1-Glcp | 43, 58, 87, 97, 117, 139 | 0.003 | →3,4,6)-Glcp-(1→ |

(6) Nuclear magnetic resonance analysis: 30 mg of *Lactarius hatsudake* Tanaka polysaccharides 1/2/3/4/5 was taken to dissolve in 1 mL of heavy water, and the resultant was put into a 5 mL test tube. The solution was transferred into a nuclear magnetic tube, and the sample was scanned using a pulse Fourier transform spectrometer. See FIG. 11, FIG. 12, FIG. 13, FIG. 14, and FIG. 15 for obtained $^1$H-NMR, $^{13}$C-NMR, $^1$H-$^1$H-COSY, HMBC, and HSQC spectrograms of LHP-1; see FIG. 16, FIG. 17, FIG. 18, FIG. 19, and FIG. 20 for spectrograms of LHP-2; see FIG. 21, FIG. 22, FIG. 23, FIG. 24, and FIG. 25 for spectrograms of LHP-3; see FIG. 26, FIG. 27, FIG. 28, FIG. 29, and FIG. 30 for spectrograms of LHP-4; and see FIG. 31, FIG. 32, FIG. 33, FIG. 34, and FIG. 35 for spectrograms of LHP-5. It can be seen from the drawings that chemical shifts of $^{13}$C and $^1$H of respective sugar residues of the *Lactarius hatsudake* Tanaka polysaccharides LHP-1/2/3/4/5 are as shown in Table 6, Table 7, Table 8, Table 9, and Table 10, which are conforming to methylation structure.

TABLE 6

Chemical Shifts of $^{13}$C and $^{1}$H of Lactarius Hatsudake Tanaka Polysaccharide LHP-1 Sugar Residue

| Sugar residue | H1 / C1 | H2 / C2 | H3 / C3 | H4 / C4 | H5 / C5 | H6 / C6 |
|---|---|---|---|---|---|---|
| →4)-α-Glcp-(1→ | 5.32 / 99.72 | 3.54 / 71.74 | 3.78 / 69.73 | 3.50 / 71.07 | 3.77 / 76.94 | 3.58 / 66.83 |
| →4,6)-α-Glcp-(1→ | 4.93 / 100.11 | 3.77 / 74.63 | 3.50 / 71.75 | 3.61 / 76.88 | 3.76 / 69.91 | 3.58 / 71.06 |
| →α-Fucp-(1→ | 5.04 / 98.47 | 3.87 / 76.99 | 3.55 / 71.59 | 3.91 / 70.47 | 3.76 / 49.91 | 1.23 / 17.41 |
| 6)-α-Galp-(1→ | 4.93 / 98.02 | 3.91 / 70.51 | 3.75 / 69.91 | 3.58 / 66.85 | 3.88 / 73.30 | 3.55 / 70.43 |
| α-Glcp-(1→ | 5.28 / 100.11 | — | — | — | — | — |
| →3,4,6)-α-Glcp-(1→ | 5.15 / 91.87 | 3.85 / 77.21 | 4.13 / 68.94 | 3.62 / 72.77 | 3.35 / 69.40 | 3.64 / 72.85 |

TABLE 7

Chemical Shifts of $^{13}$C and $^{1}$H of Lactarius Hatsudake Tanaka Polysaccharide LHP-2 Sugar Residue

| Sugar residue | H1 / C1 | H2 / C2 | H3 / C3 | H4 / C4 | H5 / C5 | H6 / C6 |
|---|---|---|---|---|---|---|
| →4)-α-Glcp-(1→ | 5.32 / 101.07 | 3.49 / 73.11 | 3.89 / 74.76 | 3.55 / 73.02 | 3.76 / 72.64 | 3.69 / 62.00 |
| Glcp-(1→ | 5.29 / 101.45 | 3.53 / 74.86 | 3.81 / 72.27 | 3.70 / 74.18 | 3.78 / 72.64 | 3.59 / 61.68 |
| →4,6)-α-Glcp-(1→ | 4.90 / 100.03 | 3.52 / 75.83 | 3.67 / 75.87 | 3.56 / 76.60 | 3.88 / 74.76 | 3.60 / 72.01 |
| →3,4)-α-Glcp-(1→ | 5.15 / 93.35 | 3.51 / 72.89 | 3.61 / 74.24 | 3.90 / 72.01 | 3.55 / 72.99 | 3.88 / 74.76 |
| →3,4,6)-α-Glcp-(1→ | 5.15 / 93.35 | 3.47 / 72.94 | 3.89 / 78.15 | 3.60 / 75.34 | 3.36 / 70.78 | 3.65 / 70.84 |
| →4)-β-Galp-(1→ | 4.57 / 97.28 | 3.21 / 75.45 | 3.68 / 77.65 | 3.77 / 78.28 | 3.84 / 78.45 | 3.70 / 74.21 |

TABLE 8

Chemical Shifts of $^{13}$C and $^{1}$H of Lactarius Hatsudake Tanaka Polysaccharide LHP-3 Sugar Residue

| Sugar residue | H1 / C1 | H2 / C2 | H3 / C3 | H4 / C4 | H5 / C5 | H6 / C6 |
|---|---|---|---|---|---|---|
| →6)-α-Galp-(1→ | 4.89 / 99.39 | 3.75 / 73.5 | 3.65 / 71.36 | 3.90 / 78.36 | 3.48 / 71.00 | 3.92 / 71.14 |
| →2,6)-α-Manp-(1→ | 4.89 / 101.50 | 3.87 / 70.36 | 3.72 / 78.48 | 3.67 / 74.29 | 3.47 / 71.07 | 3.92 / 78.36 |
| →α-Fucp-(1→ | 5.00 / 99.78 | 3.85 / 74.73 | 4.10 / 70.34 | 4.05 / 70.62 | 3.72 / 71.38 | 1.20 / 18.75 |
| →4)-α-Glcp-(1→ | 5.29 / 101.05 | 3.58 / 86.08 | 4.12 / 70.19 | 3.59 / 71.22 | 3.80 / 68.53 | 3.91 / 67.23 |
| α-Glcp-(1→ | 4.84 / 101.05 / 5.27 / 101.26 | 3.79 / 70.92 | 3.46 / 71.00 | 3.74 / 73.55 | 3.55 / 68.21 | 3.84 / 61.35 |

TABLE 9

Chemical Shifts of $^{13}$C and $^{1}$H of Lactarius Hatsudake Tanaka Polysaccharide LHP-4 Sugar Residue

| Sugar residue | H1 / C1 | H2 / C2 | H3 / C3 | H4 / C4 | H5 / C5 | H6 / C6 |
|---|---|---|---|---|---|---|
| →6)-α-Galp-(1→ | 4.88 / 99.43 | 3.74 / 70.85 | 3.46 / 71.04 | 3.91 / 71.32 | 3.64 / 71.29 | 3.88 / 78.28 |
| →2,6)-α-Manp-(1→ | 4.88 / 101.4 | 3.86 / 71.05 | 4.10 / 70.19 | 3.56 / 68.14 | 3.80 / 68.15 | 3.90 / 71.27 |
| →α-Fucp-(1→ | 4.99 / 100.10 | 3.85 / 74.67 | 3.52 / 73.52 | 4.04 / 73.34 | 3.72 / 70.85 | 1.20 / 18.70 |
| →4)-α-Glcp-(1→ | 5.27 / 101.01 | 3.46 / 71.04 | 3.73 / 73.46 | 3.38 / 76.88 | 3.64 / 71.28 | 3.89 / 73.31 |
| →3)-α-Glcp-(1→ | 4.82 / 101.00 | 3.79 / 70.58 | 3.57 / 73.94 | 3.72 / 70.85 | 4.05 / 70.55 | 3.82 / 62.11 |
| α-Glcp-(1→ | 5.24 / 101.13 | — | — | — | — | — |
| →6)-β-Glcp-(1→ | 4.41 / 104.41 | 3.19 / 74.57 | 3.53 / 75.95 | 3.33 / 70.87 | 3.63 / 74.04 | 4.02 / 70.79 |

TABLE 10

Chemical Shifts of $^{13}$C and $^{1}$H of Lactarius Hatsudake Tanaka Polysaccharide LHP-5 Sugar Residue

| Sugar residue | H1 / C1 | H2 / C2 | H3 / C3 | H4 / C4 | H5 / C5 | H6 / C6 |
|---|---|---|---|---|---|---|
| →3)-α-Glcp-(1→ | 4.62 / 104.15 | 3.30 / 74.47 | 3.67 / 85.23 | 3.43 / 73.90 | 3.83 / 76.39 | 3.41 / 70.72 |
| →6)-β-Glcp-(1→ | 4.44 / 104 | 3.25 / 74.41 | 3.42 / 76.78 | 3.67 / 74.12 | 3.85 / 70.85 | 3.67 / 85.23 |
| →3,6)-β-Glcp-(1→ | 5.15 / 93.11 | 3.65 / 86.06 | 3.44 / 85.23 | 3.67 / 74.12 | 3.85 / 70.95 | 3.36 / 69.75 |
| →2,6)-α-Manp-(1→ | 4.92 / 99.23 | 3.90 / 71.66 | 3.49 / 74.24 | 3.94 / 71.25 | 3.84 / 67.69 | 3.42 / 69.54 |
| →6)-α-Galp-(1→ | 4.92 / 101.3 | 3.90 / 71.66 | 3.49 / 74.24 | 3.94 / 71.25 | 3.84 / 67.96 | 3.42 / 69.54 |
| α-Glcp-(1→ | 5.26 / 101.63 | 4.01 / 79.63 | 3.91 / 74.33 | 3.73 / 77.05 | 3.60 / 75.88 | 3.84 / 67.95 |
| →4)-β-Glcp-(1→ | 5.31 / 100.89 | 3.56 / 75.96 | 3.71 / 71.38 | 4.10 / 70.13 | 3.54 / 71.36 | 3.77 / 61.77 |
| →α-Fucp-(1→ | 5.03 / 99.58 | 3.87 / 74.41 | 4.13 / 70.02 | 3.60 / 67.98 | 3.76 / 70.74 | 1.23 / 18.59 |

After the above structural characterization of THE Lactarius hatsudake Tanaka polysaccharides LHP-1/2/3/4/5, analysis is as follows.

$^{1}$H and $^{13}$C NMR spectrograms of the LHP-1 component have 6 main peaks in anomeric proton (4.3-5.2 ppm) and anomeric carbon (90-110 ppm) regions. Combined with methylation and monosaccharide composition results, relatively strong signals 5.32/99.72, 4.93/100.11 and 5.04/98.47 respectively belong to →4)-α-Glcp-(1→, →4,6)-α-Glcp-(1→ and →α-Fucp-(1→, and the remaining weak signals 4.93/98.02, 5.28/100.11 and 5.15/91.87 belong to →6)-α-Galp-(1→, α-Glcp-(1→ and →3,4,6)-α-Glcp-(1→. Resonance peak of corresponding proton was then found according to HSQC and 13C. HMBC diagram shows that cross peaks 5.32/71.07 and 3.50/99.72 indicate that H-1 of →4)-α-Glcp-(1→ has a coupling relationship with C-4 and H-4 of C-1, cross peak 3.61/99.72 indicates that C-1 of →4)-α-Glcp-(1→ and H4 of →4,6)-α-Glcp-(1→ have a coupling relationship, as main chains of this component. In addition, cross peak 5.04/71.06 indicates that H-1 of →α-Fucp-(1→ and C-6 of →4,6)-α-Glcp-(1→ have a coupling relationship. Cross peaks 4.93/70.43 and 4.93/71.06 indicate that H1 of →6)-α-Galp-(1→ is coupled with C-6 of →4,6)-α-Glcp-(1→ and →6)-α-Galp-(1→.

In combination with the above results, a structural formula of the *Lactarius hatsudake* Tanaka polysaccharide LHP-1 is:

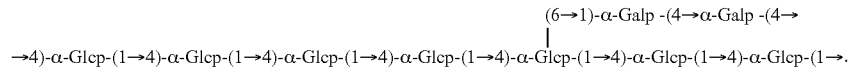

¹H and ¹³C NMR spectrograms of the LHP-2 component have 6 main peaks in anomeric proton (4.3-5.2 ppm) and anomeric carbon (90-110 ppm) regions. Combined with methylation and monosaccharide composition results, relatively strong signals 5.32/101.07, 5.29/101.45, and 4.90/100.03 respectively belong to →4)-α-Glcp-(1→, Glcp-(1→ and →4,6)-α-Glcp-(1→, and the remaining weak signals 5.15/93.35, 5.15/93.35, and 4.57/97.28 belong to →3,4)-α-Glcp-(1→, →3,4,6)-α-Glcp-(1→ and →4)-β-Galp-(1→. Resonance peak of corresponding proton was then found according to HSQC and 13C. The cross peaks in HMBC spectrogram 5.32/73.02, 5.32/76.60, 5.32/72.02, and 5.32/78.35 indicate that H-1 of →4)-α-Glcp-(1→ is coupled with C-4 of →4)-α-Glcp-(1→, →4,6)-α-Glcp-(1→ and →3,4)-α-Glcp-(1→ and C-3 of →3,4,6)-α-Glcp-(1→, cross peak 5.29/72.01 indicates that H-1 of Glcp-(1→ and C-6 of →4,6)-α-Glcp-(1→ are coupled, and cross peak 4.57/76.33 indicates that H-1 of →4)-β-Galp-(1→ and C-3 of →3,4)-α-Glcp-(1→ are coupled.

In combination with the above results, a structural formula of the *Lactarius hatsudake* Tanaka polysaccharide LHP-2 is:

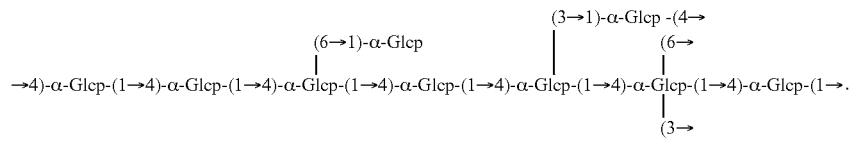

¹H and ¹³C NMR spectrograms of the LHP-3 component have 6 main peaks in anomeric proton (4.3-5.2 ppm) and anomeric carbon (90-110 ppm) regions. Combined with methylation and monosaccharide composition results, relatively strong signals 4.89/99.39, 4.89/101.50 and 5.00/99.783 respectively belong to →6)-α-Galp-(1→, →2,6)-α-Manp-(1→ and →α-Fucp-(1→, and the remaining weak signals 5.29/101.05, 4.84/101.05 and 5.27/101.26 belong to →4)-α-Glcp-(1→, →3)-α-Glcp-(1→ and α-Glcp-(1→. Resonance peak of corresponding proton was then found according to HSQC and 13C. The cross peaks in HMBC spectrogram 4.89/71.14 and 4.89/78.36 indicate that H-1 of →6)-α-Galp-(1→ is coupled with C-6 of →6)-α-Galp-(1→ and C-6 of →2,6)-α-Manp-(1→, cross peak 5.00/70.36 indicates that H-1 of →α-Fucp-(1→ and C-2 of →2,6)-α-Manp-(1→ are coupled, and cross peak 4.84/70.36 indicates that H-1 of →3)-α-Glcp-(1→ and C-2 of →2,6)-α-Manp-(1→ are coupled.

In combination with the above results, a structural formula of the *Lactarius hatsudake* Tanaka polysaccharide LHP-3 is:

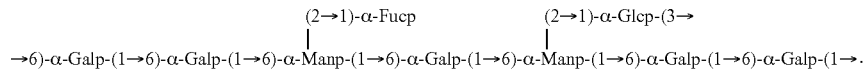

¹H and ¹³C NMR spectrograms of the LHP-4 component have 7 main peaks in anomeric proton (4.3-5.2 ppm) and anomeric carbon (90-110 ppm) regions. Combined with methylation and monosaccharide composition results, relatively strong signals 4.88/99.34, 4.88/101.4 and 4.99/100.10 respectively belong to →6)-α-Galp-(1→, →2,6)-α-Manp-(1→ and α-Fucp-(1→, and the remaining weak signals 5.27/101.01, 4.82/101.00, 5.24/101.13 and 4.41/104.41 belong to →4)-α-Glcp-(1→, →3)-α-Glcp-(1→, α-Glcp-(1→ and →6)-β-Glcp-(1→. Resonance peak of corresponding proton was then found according to HSQC and 13C. The cross peaks in HMBC spectrogram 4.88/78.28, and 4.88/71.27 indicate that H-1 of →6)-α-Galp-(1→ is coupled with C-6 of →6)-α-Galp-(1→ and C-6 of →2,6)-α-Manp-(1→, cross peak 4.89/78.28 indicates that H-1 of α-Fucp-(1→ and C-2 of →2,6)-α-Manp-(1→ are coupled, cross peaks 3.86/101.01, 3.86/100.00, and 3.86/101.03 indicate that H-2 of →2,6)-α-Manp-(1→ is coupled with C-1 of →4)-α-Glcp-(1→, →3)-α-Glcp-(1→ and α-Glcp-(1→, and cross peak 3.38/104.41 indicates that H-4 of →4)-α-Glcp-(1→ and C-1 of →6)-β-Glcp-(1→ are coupled.

In combination with the above results, a structural formula of the *Lactarius hatsudake* Tanaka polysaccharide LHP-4 is:

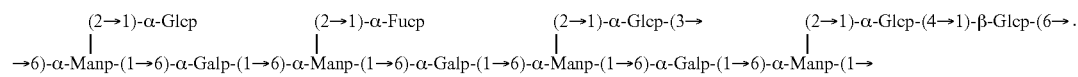

$^1$H and $^{13}$C NMR spectrograms of the LHP-5 component have 8 main peaks in anomeric proton (4.3-5.2 ppm) and anomeric carbon (90-110 ppm) regions. Combined with methylation and monosaccharide composition results, relatively strong signals 4.62/104.15, 4.44/104 and 5.15/93.11 respectively belong to →3)-α-Glcp-(1→, →6)-β-Glcp-(1→ and →3,6)-β-Glcp-(1→, the remaining weak signals 4.92/99.23, 4.92/101.3 and 5.26/101.63, 5.31/100.89 and 5.03/99.58 belong to →2,6)-α-Manp-(1→, →6)-α-Galp-(1→, α-Glcp-(1→, →4)-α-Glcp-(1→ and α-Fucp-(1→. Resonance peak of corresponding proton was then found according to HSQC and 13C. The cross peak in HMBC spectrogram 4.62/85.23 indicates that H-1 of →3)-α-Glcp-(1→ and C-3 of →3)-α-Glcp-(1→ and →3,6)-β-Glcp-(1→ are coupled, cross peaks 3.36/100.40 and 3.67/100.40 indicate that C-1 of →6)-β-Glcp-(1→ and H-6 of →3,6)-β-Glcp-(1→ and →2,6)-α-Manp-(1→ are coupled, cross peaks 5.03/71.38 and 4.92/71.38 indicate that C-2 of →2,6)-α-Manp-(1→ and H-1 of →6)-α-Galp-(1→ and Fucp-(1→ are coupled.

In combination with the above results, a structural formula of the *Lactarius hatsudake* Tanaka polysaccharide LHP-5 is:

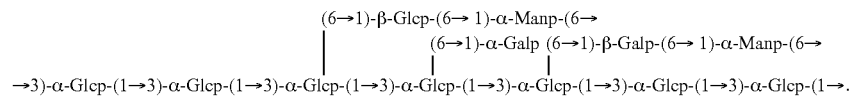

In order to investigate relevant effects of the resulting *Lactarius hatsudake* Tanaka polysaccharide mixture and the *Lactarius hatsudake* Tanaka polysaccharides LHP-1/2/3/4/5, the following experiment was specifically carried out.

Figure 36:
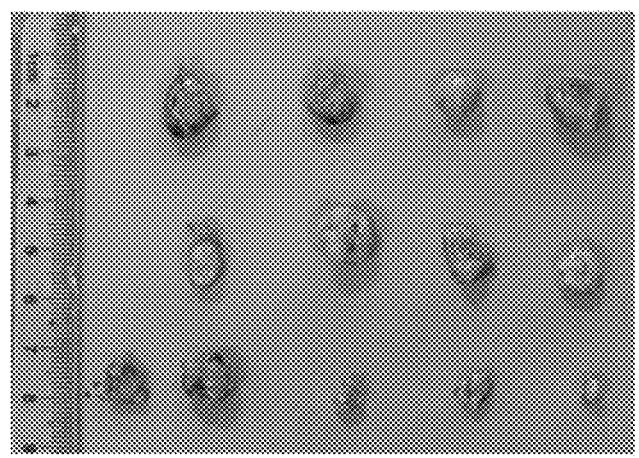
FIG. 36 is a photograph of tumor volume change of mice in an experiment of *Lactarius hatsudake* Tanaka polysaccharide mixture inhibiting tumor growth in HepG2 tumor-bearing mice.
Figure 37:
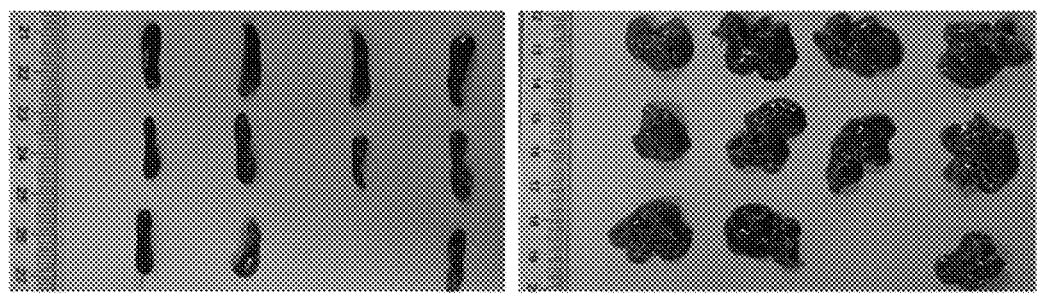
FIG. 37 is a photograph of organs of mice in the experiment of *Lactarius hatsudake* Tanaka polysaccharide mixture inhibiting tumor growth in HepG2 tumor-bearing mice.

1. Experiment of *Lactarius hatsudake* Tanaka Polysaccharide Mixture LHP Inhibiting Tumor Growth in HepG2 Tumor-Bearing Mice Male BALB/C nude mice (4-5 weeks old) (SPF grade) were selected, and kept under standard conditions (25±2° C., 60±5% humidity, 12 h light/dark cycle), with free access to food and water. After one week of acclimatization, the mice started to be modelled. HepG2 cell cryopreservation tube was taken from liquid nitrogen, and rapidly placed in 37° C. water bath and gently shaken, to make the cells to be rapidly thawed completely. An outer surface of the cryopreservation tube was wiped with 75% alcohol in a super clean bench, with sterile operation, a sealing film was removed, a tube cover was opened, and a cell suspension was sucked out by a pipette, placed in a 15 mL BD centrifuge tube, and supplemented to about 10 mL with physiological saline. Suspended cells were gently blown evenly by the pipette, and centrifuged at 800 r/min for 10 min, and supernatant was discarded. The above washing process was repeated twice, and cells were uniformly suspended by an appropriate amount of physiological saline, and counted, each mouse was injected with $1\times10^7$ cells, the mice were inoculated with the cells into abdominal cavity according to 0.2 mL per mouse under aseptic condition, and when the tumor volume reached 100 mm$^3$, the models were successfully made. Experimental mice were divided into 3 groups, including model group intragastrically administered with physiological saline, and polysaccharide intervention groups (with doses of 250 and 500 mg/kg respectively), with 5 mice in each group. Body weight of each mouse was weighed before the experiment. During the experiment, the mice were fed normally, and the body weight and tumor volume were weighed, as shown in Table 11 and FIG. 36. Compared with control group, the tumor volume was obviously reduced. The experimental groups were intragastrically administered with corresponding dose of polysaccharide samples, and dissected after 17 days, to take organs such as liver, spleen, thymus, and colon as shown in Table 12 and FIG. 37. Compared with the control group, liver pathological conditions were reduced, and spleen was reduced.

TABLE 11

Influence of Polysaccharide on Tumor Volume in HepG2 Tumor-bearing Mice (x ± s, n = 5)

| Group | Tumor volume (mm$^3$) | | | | | | |
|---|---|---|---|---|---|---|---|
| | D1 | D4 | D7 | D10 | D13 | D16 | D17 |
| Model control group | 104.76 ± 60.93 | 143.77 ± 79.84 | 219.85 ± 90.61 | 268.63 ± 86.47 | 292.56 ± 77.48 | 686.76 ± 359.61 | 652.37 ± 176.88 |
| Polysaccharide | 102.71 ± | 89.48 ± | 211.41 ± | 158.93 ± | 138.73 ± | 243.19 ± | 334.22 ± |

TABLE 11-continued

Influence of Polysaccharide on Tumor Volume in HepG2 Tumor-bearing Mice (x ± s, n = 5)

| | Tumor volume (mm³) | | | | | | |
|---|---|---|---|---|---|---|---|
| Group | D1 | D4 | D7 | D10 | D13 | D16 | D17 |
| intervention low dose group | 42.52 | 46.66 | 87.45 | 79.56* | 72.04** | 102.85* | 220.29* |
| Polysaccharide intervention high dose group | 103.28 ± 48.87 | 41.64 ± 6.66** | 174.02 ± 89.78 | 118.15 ± 24.95** | 102.59 ± 18.18** | 145.95 ± 69.52** | 135.12 ± 59.42** |

Note: compared with the model control group, *P≤0.05, **P≤0.01.

TABLE 12

Influence of Polysaccharide on Viscera-to-Body Ratio of Tumor, Liver, and Spleen of HepG2 Tumor-bearing Mice (x ± s, n = 5)

| Group | Tumor-to-body ratio (%) | Liver-to-body ratio (%) | Spleen-to-body ratio (%) |
|---|---|---|---|
| Model control group | 3.123 ± 0.887 | 6.541 ± 0.630 | 0.879 ± 0.083 |
| Polysaccharide intervention low dose group | 2.398 ± 0.892 | 6.382 ± 0.541 | 0.629 ± 0.221* |
| Polysaccharide intervention high dose group | 1.298 ± 0.854* | 6.670 ± 0.170 | 0.715 ± 0.044 |

Note:
compared with the model control group,
*P ≤ 0.05; x ± s, n = 5.

Figure 38:
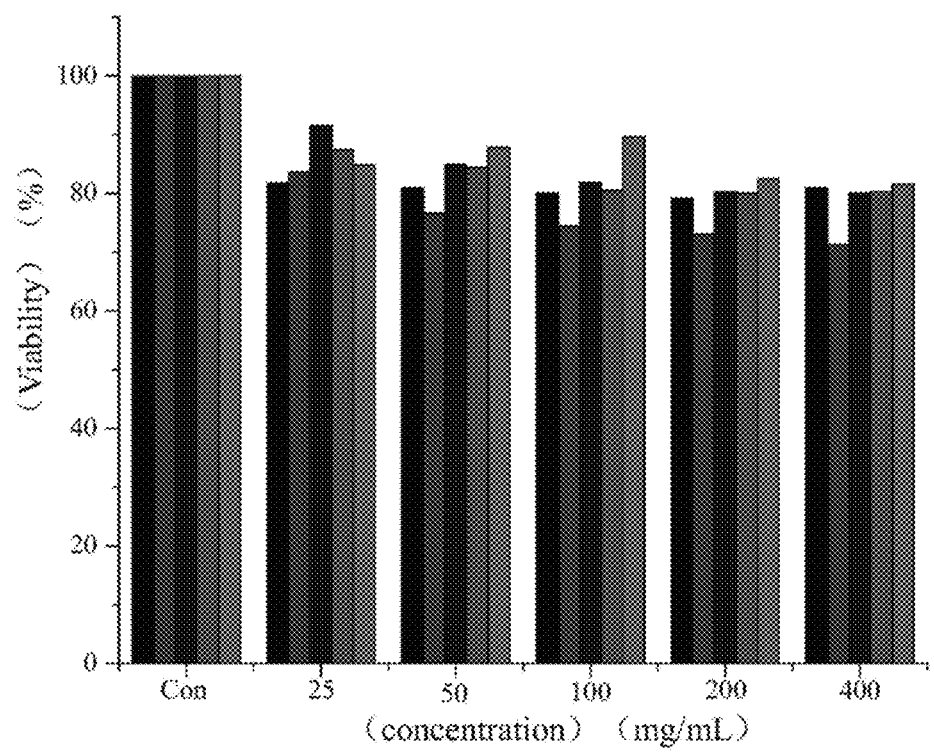
FIG. 38 is a histogram of cell viability.

2. Experiment of the *Lactarius hatsudake* Tanaka Polysaccharides LHP-1/2/3/4/5 Inhibiting Cancer Cell Growth Experimental Process of the *Lactarius hatsudake* Tanaka Refined Polysaccharide LHP and LHP-1/2/3/4/5 on HepG2 Cells Cell proliferation experiment: after recovery, HepG2 cells were cultured in DMEM/1640 culture medium containing 10% PBS, and placed in an incubator under condition of 37° C. and 5% $CO_2$. When HepG2 cells overgrew the bottom of cell culture dish, 1 mL of pancreatin was added, and the pancreatin was removed after cell digestion. After the culture medium was added, the resultant was blown, and counted with a blood cell counter plate, and about 70-80% of the original culture medium was sucked out. 100 μL of DMEM culture media containing the *Lactarius hatsudake* Tanaka polysaccharides LHP-1/2/3/4/5 with concentration of 0, 25, 50, 100, 200, and 400 μg/mL were added into a 96-well plate, for incubation at 37° C. for 24 h. 10 μL of MTS reagent was then added to each well for incubation for 30 min. Absorbance at 490 nm was measured using a plate reader. Cell viability was calculated, and results are as shown in FIG. 38 (columns in the histogram represent LHP-1/2/3/4/5 from left to right in sequence).

Example 2

Different from Example 1, the water extraction temperature was 90° C., the dialysis in the deproteinization process lasted for 3 days, and time of the JK008 macroporous resin adsorption was 10 h.

Example 3

Different from Example 1, the water extraction temperature was 100° C., and time of the JK008 macroporous resin adsorption was 12 h.

Comparative Example 1

For the process of polysaccharide purification, JK008 was selected as the resin, with purity of 85-90%, and purity obtained in an earlier stage with resin D941 was merely 73%.

During ethanol fractionation, concentration of polysaccharide was 5 mg/mL, and the concentration was too high, such that 10% part was hard gel, and could not be separated.

Comparative Example 2

Different from Example 1, in the alcohol precipitation purification in step (2), only 40%, 60%, and 80% anhydrous ethanol system was used.

In this system, due to the lack of treatment with 10% concentration, 40% component was colloidal, complex with multiple peaks obtained by gel chromatography column in cooperation with liquid phase scanning diagram cannot form a single peak shape like 40% component in Example 1, and finally LHP-2 component could not be obtained.

Comparative Example 3

Different from Example 1, in the alcohol precipitation purification in step (2), only 30%, 40%, 50%, 60%, and 70% anhydrous ethanol system was used.

Under this system, it was found that 30% component almost occupied 80-90% of refined polysaccharides, and composition thereof was complex and poor in uniformity, resulting in a very small amount of the following four components, such that separation effect of the whole polysaccharides was poor, and the next-step separation via liquid chromatogram could not be carried out.

By analyzing the alcohol precipitation system, it can be found that establishment of 10%, 40%, 60%, and 80% systems is crucial for separation of the 5 target compounds, and meanwhile also has a great influence on their purity. In the above, the use of anhydrous ethanol with 10% concentration is the key to the subsequent effective separation of 40%, 60%, and 80% alcohol precipitation products.

Finally, it should be indicated that the various examples above are merely used for illustrating the technical solutions of the present disclosure, rather than limiting the present disclosure; while the detailed description is made to the present disclosure with reference to the various preceding examples, those ordinarily skilled in the art should understand that they still could modify the technical solutions recited in the various preceding examples, or make equivalent substitutions to some or all of the technical features therein; and these modifications or substitutions do not make the essence of the corresponding technical solutions depart from the scope of the technical solutions of the various examples of the present disclosure.

What is claimed is:

1. A method for extracting a *Lactarius hatsudake* Tanaka polysaccharide compound, comprising:

carrying out freeze-drying, pulverization, degreasing, water extraction, deproteinization, alcohol precipitation, and resin adsorption in sequence on *Lactarius hatsudake* Tanaka fruiting bodies to obtain a *Lactarius hatsudake* Tanaka refined polysaccharide mixture, wherein the resin adsorption comprises: dissolving a solid obtained from the alcohol precipitation in water, then adding activated JK008 macroporous resin, stirring and adsorbing a mixture for 6-12 h, after solid-liquid separation, centrifuging for a liquid to remove insolubles, followed by reduced-pressure distillation, secondary alcohol precipitation, and freeze-drying to obtain the *Lactarius hatsudake* Tanaka refined polysaccharide mixture;

to the *Lactarius hatsudake* Tanaka refined polysaccharide mixture, adding anhydrous ethanol dropwise to perform alcohol precipitation purification, and gradually collecting precipitates with an ethanol volume concentration of 10%, 40%, 60%, and 80%, to obtain *Lactarius hatsudake* Tanaka polysaccharide-10/40/60/80 active ingredients, wherein a concentration of the *Lactarius hatsudake* Tanaka refined polysaccharide mixture is less than 5 mg/mL; and performing preparation via liquid chromatography on the *Lactarius hatsudake* Tanaka polysaccharide-10/40/60/80 active ingredients respectively, followed by dialysis and post-treatment to obtain *Lactarius hatsudake* Tanaka polysaccharide LHP-1, *Lactarius hatsudake* Tanaka polysaccharide LHP-2, *Lactarius hatsudake* Tanaka polysaccharide LHP-3, *Lactarius hatsudake* Tanaka polysaccharide LHP-4, and *Lactarius hatsudake* Tanaka polysaccharide LHP-5, wherein a condition of the preparation via liquid chromatography comprises: an injection volume is 1 mL, a chromatography column is SUGAR-BRT-102 gel chromatography column, a column temperature is 35° C., a column length is 28 cm, a flow rate is 1.3 mL/min, and a mobile phase is 0.2 mol/L aqueous sodium chloride solution;

a structural formula of the *Lactarius hatsudake* Tanaka polysaccharide LHP-1 is:

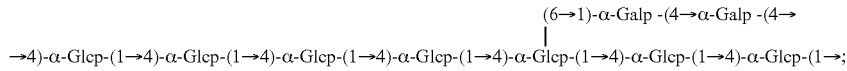

a structural formula of the *Lactarius hatsudake* Tanaka polysaccharide LHP-2 is:

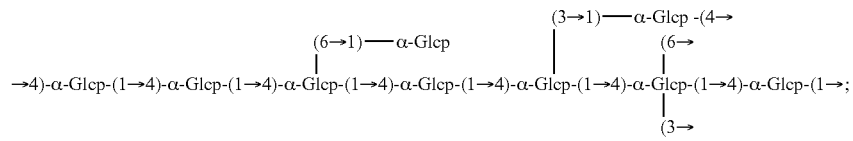

a structural formula of the *Lactarius hatsudake* Tanaka polysaccharide LHP-3 is:

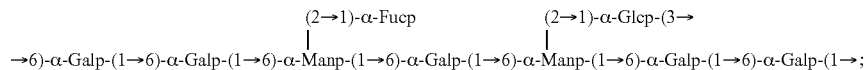

a structural formula of the *Lactarius hatsudake* Tanaka polysaccharide LHP-4 is:

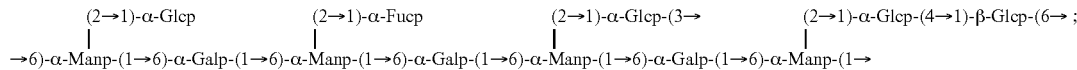

a structural formula of the *Lactarius hatsudake* Tanaka polysaccharide LHP-5 is:

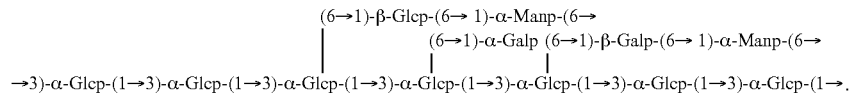

2. The method according to claim 1, satisfying at least one of following conditions:
   a. the freeze-drying is performed at a temperature of −80° C. for 2-3 d;
   b. particles obtained from the pulverization have a particle size less than or equal to 60 mesh;
   c. the degreasing comprises: repeatedly soaking the particles obtained from the pulverization using anhydrous ethanol, and collecting a solid after solid-liquid separation, drying the solid and then pulverizing a dried solid again, and sieving a resultant with a 60-mesh sieve to obtain a pretreated *Lactarius hatsudake* Tanaka freeze-dried powder; and
   d. the water extraction comprises: mixing a degreased solid with water, treating a mixture under a condition of 85-100° C. for 3 h, after solid-liquid separation, repeating foregoing operations on a solid, combining liquids to obtain a crude polysaccharide aqueous solution, and concentrating the crude polysaccharide aqueous solution to obtain a concentrated crude polysaccharide aqueous solution.

3. The method according to claim 1, wherein the deproteinization comprises: treating a solution obtained from the water extraction with papain and a Sevag reagent, placing a liquid into an 8000-14000 Da dialysis bag to stand at 4° C. for 2-3 days, during which time water is changed every 2 h, and after dialysis, concentrating a resultant to obtain a deproteinized concentrated solution.

4. The method according to claim 1, wherein the alcohol precipitation comprises: to a solution obtained from the deproteinization, adding 4 times volume of ethanol dropwise, followed by standing and centrifuging to obtain a polysaccharide precipitate, and re-dissolving the precipitate by adding water, followed by concentrating under reduced pressure, and freeze-drying to obtain *Lactarius hatsudake* Tanaka secondary polysaccharide.

5. The method according to claim 1, wherein in a process of performing the alcohol precipitation purification, after dropwise addition for each concentration gradient is finished, a resultant is stood for 12 h at 4° C., and centrifuged to obtain a precipitate.

6. The method according to claim 5, wherein the precipitate is re-dissolved by adding water, then concentrated under reduced pressure and freeze-dried to obtain the *Lactarius hatsudake* Tanaka polysaccharide-10/40/60/80 active ingredients.

7. The method according to claim 1, before performing the preparation via liquid chromatography, the method further comprises:
   mixing the *Lactarius hatsudake* Tanaka polysaccharide-10/40/60/80 active ingredients respectively with water, and undergoing 60° C. water bath for 30 min, followed by vortex blending, and filtration with a 0.45 μm water film, to obtain corresponding samples.

8. The method according to claim 1, wherein the dialysis comprises: performing dialysis for 2 d using a 7000 Da dialysis bag.

9. The method according to claim 1, wherein the post-treatment comprises: performing rotary evaporation and freeze-drying on a polysaccharide solution obtained after the dialysis to obtain a corresponding compound.

* * * * *